US012667338B2

(12) United States Patent
Huang et al.

(10) Patent No.: US 12,667,338 B2
(45) Date of Patent: Jun. 30, 2026

(54) HIGH-SENSITIVITY AND REAL-TIME ULTRASOUND BLOOD FLOW IMAGING BASED ON ADAPTIVE AND LOCALIZED SPATIOTEMPORAL CLUTTER FILTERING

(71) Applicant: Mayo Foundation for Medical Education and Research, Rochester, MN (US)

(72) Inventors: Chengwu Huang, Rochester, MN (US); Shigao Chen, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 117 days.

(21) Appl. No.: 17/799,321

(22) PCT Filed: Feb. 11, 2021

(86) PCT No.: PCT/US2021/017631
§ 371 (c)(1),
(2) Date: Aug. 12, 2022

(87) PCT Pub. No.: WO2021/163307
PCT Pub. Date: Aug. 19, 2021

(65) Prior Publication Data
US 2023/0086332 A1 Mar. 23, 2023

Related U.S. Application Data

(60) Provisional application No. 62/975,515, filed on Feb. 12, 2020.

(51) Int. Cl.
*A61B 8/00* (2006.01)
*A61B 8/06* (2006.01)
*G01S 15/89* (2006.01)

(52) U.S. Cl.
CPC .............. *A61B 8/5207* (2013.01); *A61B 8/06* (2013.01); *A61B 8/5269* (2013.01); *G01S 15/8915* (2013.01)

(58) Field of Classification Search
CPC ......... A61B 8/06; A61B 8/488; A61B 8/5269; G01S 15/8981
See application file for complete search history.

(56) References Cited

U.S. PATENT DOCUMENTS 5,477,858 A * 12/1995 Norris ................. G01S 7/52069
600/455
5,494,037 A 2/1996 Banjanin et al.
(Continued)

FOREIGN PATENT DOCUMENTS

WO 2017/146886 A1 8/2017
WO 2021/163307 A1 8/2021

OTHER PUBLICATIONS

C. Demene et al, "Spatiotemporal Clutter Filtering of Ultrafast Ultrasound Data Highly Increases Doppler and fUltrasound Sensitivity", IEEE Transactions on Medical Imaging, vol. 34, No. 11, pp. 2271-2285, Nov. 2015 (Year: 2015).*
(Continued)

*Primary Examiner* — Nyrobi Celestine
(74) *Attorney, Agent, or Firm* — Quarles & Brady LLP

(57) ABSTRACT

Described here are systems and methods for ultrasound clutter filtering to produce images of blood flow in a subject. The systems and methods described in the present disclosure may be advantageously applied to fast ultrasound imaging techniques, including ultrafast plane wave imaging techniques.

12 Claims, 14 Drawing Sheets

(56)　　　　References Cited

U.S. PATENT DOCUMENTS

| | | | | |
|---|---|---|---|---|
| 8,098,910 | B2 | 1/2012 | Srinivasan | |
| 8,992,429 | B2 * | 3/2015 | Sato | G01S 15/8981 |
| | | | | 600/453 |
| 2005/0004462 | A1 * | 1/2005 | Sakaguchi | A61B 8/06 |
| | | | | 600/441 |
| 2008/0107321 | A1 * | 5/2008 | Oh | G06T 7/0012 |
| | | | | 382/132 |
| 2008/0242982 | A1 * | 10/2008 | Tamura | A61B 8/06 |
| | | | | 600/441 |
| 2009/0141957 | A1 * | 6/2009 | Yen | G01S 15/8977 |
| | | | | 600/437 |
| 2011/0301470 | A1 * | 12/2011 | Sato | A61B 8/13 |
| | | | | 600/463 |
| 2012/0078107 | A1 * | 3/2012 | Ma | A61B 8/06 |
| | | | | 600/454 |
| 2018/0220997 | A1 * | 8/2018 | Song | G16H 50/30 |
| 2018/0271498 | A1 * | 9/2018 | Guenther | G01S 7/52046 |
| 2019/0083068 | A1 * | 3/2019 | Sornes | A61B 8/5253 |
| 2019/0167118 | A1 * | 6/2019 | Vilenskii | A61B 5/021 |
| 2019/0223828 | A1 * | 7/2019 | Torp | A61B 8/5207 |
| 2019/0369220 | A1 * | 12/2019 | Vignon | A61B 8/54 |
| 2020/0081107 | A1 * | 3/2020 | Shin | G01S 7/52047 |
| 2020/0200886 | A1 * | 6/2020 | Vignon | G01S 7/52025 |

OTHER PUBLICATIONS

C. Huang et al, "Noninvasive Contrast-Free 3D Evaluation of Tumor Angiogenesis with Ultrasensitive Ultrasound Microvessel Imaging", Scientific Reports, vol. 9, pp. 1-11, Oct. 2018 (Year: 2018).*

J. Baranger et al, "Adaptive Spatiotemporal SVD Clutter Filtering for Ultrafast Doppler Imaging Using Similarity of Spatial Singular Vectors", IEEE Transactions on Medical Imaging, vol. 37, No. 7, pp. 1574-1586, Jul. 2018 (Year: 2018).*

C. Huang et al, "Debiasing-Based Noise Suppression for Ultrafast Ultrasound Microvessel Imaging", IEEE Transactions on Ultrasonics, Ferroelectrics, and Frequency Control, vol. 66, No. 8, pp. 1281-1291, Aug. 2019 (Year: 2019).*

International Search Report of related PCT/US2021/017631, mailed on Jul. 13, 2021, 5 pages.

Written Opinion of related PCT/US2021/017631, mailed on Jul. 13, 2021, 7 pages.

Song, P., Manduca, A., Trzasko, J. D., & Chen, S. (2016). Ultrasound small vessel imaging with block-wise adaptive local clutter filtering. IEEE transactions on medical imaging, 36(1), 251-262.

Song, P., Trzasko, J. D., Manduca, A., Qiang, B., Kadirvel, R., Kallmes, D. F., & Chen, S. (2017). Accelerated singular value-based ultrasound blood flow clutter filtering with randomized singular value decomposition and randomized spatial downsampling. IEEE transactions on ultrasonics, ferroelectrics, and frequency control, 64(4), 706-716.

Song, P., Manduca, A., Trzasko, J. D., & Chen, S. (2017). Noise equalization for ultrafast plane wave microvessel imaging. IEEE transactions on ultrasonics, ferroelectrics, and frequency control, 64(11), 1776-1781.

Alfred, C. H., & Lovstakken, L. (2010). Eigen-based clutter filter design for ultrasound color flow imaging: A review. IEEE transactions on ultrasonics, ferroelectrics, and frequency control, 57(5), 1096-1111.

Kruse, D. E., & Ferrara, K. W. (2002). A new high resolution color flow system using an eigendecomposition-based adaptive filter for clutter rejection. IEEE transactions on ultrasonics, ferroelectrics, and frequency control, 49(10), 1384-1399.

Baranger, J., Arnal, B., Perren, F., Baud, O., Tanter, M., & Demené, C. (2018). Adaptive spatiotemporal SVD clutter filtering for ultrafast Doppler imaging using similarity of spatial singular vectors. IEEE transactions on medical imaging, 37(7), 1574-1586.

Lovstakken, L., Bjaerum, S., Kristoffersen, K., Haaverstad, R., & Torp, H. (2006). Real-time adaptive clutter rejection filtering in color flow imaging using power method iterations. IEEE transactions on ultrasonics, ferroelectrics, and frequency control, 53(9), 1597-1608.

Huang, C., Song, P., Gong, P., Trzasko, J. D., Manduca, A., & Chen, S. (2019). Debiasing-based noise suppression for ultrafast ultrasound microvessel imaging. IEEE transactions on ultrasonics, ferroelectrics, and frequency control, 66(8), 1281-1291.

* cited by examiner

SINGULAR VALUE CURVE

CURVATURE OF THE SINGULAR VALUE CURVE

WEIGHTING FUNCTION $1/\sigma_i^2$

SINGULAR VALUE ORDER

WINDOW FUNCTION WIN(i)

SINGULAR VALUE ORDER

WEIGHTING FUNCTION $wt_i = \dfrac{1}{\sigma_i^2} WIN(i)$

SINGULAR VALUE ORDER

A SET OF FOUR GAUSSIAN WINDOWS CENTERED AT FOUR DIFFERENT POSITIONS

A SET OF FOUR SQUARE WINDOWS CENTERED AT FOUR DIFFERENT POSITIONS

FINAL BLOOD FLOW IMAGE COMBINED FROM
THE FOUR SEPARATE BLOOD FLOW IMAGES

FOUR BLOOD FLOW IMAGES OBTAINED FROM FOUR WEIGHTED ULTRASOUND DATA

HIGH-SENSITIVITY AND REAL-TIME ULTRASOUND BLOOD FLOW IMAGING BASED ON ADAPTIVE AND LOCALIZED SPATIOTEMPORAL CLUTTER FILTERING

CROSS-REFERENCE TO RELATED APPLICATIONS

This application represents the national stage entry of PCT/US2021/017631 filed on Feb. 11, 2021 and claims the benefit of U.S. Provisional Patent Application Ser. No. 62/975,515, filed on Feb. 12, 2020, and entitled "HIGH-SENSITIVITY AND REAL-TIME ULTRASOUND BLOOD FLOW IMAGING BASED ON ADAPTIVE AND LOCALIZED SPATIOTEMPORAL CLUTTER FILTER-ING," the contents of which are incorporated herein by reference as if set forth in its entirety for all purposes.

STATEMENT REGARDING FEDERALLY SPONSORED RESEARCH

This invention was made with government support under DK120559 awarded by the National Institutes of Health. The government has certain rights in the invention.

BACKGROUND

The development of software beamforming-based ultrasound systems and high frame rate ultrasound imaging method, such as plane wave imaging and diverging wave imaging, has allowed collection of larger amount of spatial-temporal ultrasound data in a short period of time, which significantly boosted the sensitivity to small vessel in ultrasound blood flow Doppler imaging. Recently, the combination of high frame rate ultrasound imaging and advanced eigen-based spatial-temporal clutter filtering, such as singular value decomposition (SVD) clutter filtering and eigenvalue decomposition (EVD) clutter filtering, enables better separation of tissue clutters and blood flow signals by leveraging both the temporal and spatial information from the larger amount ultrasound data. These techniques have been demonstrated with superior performance in small vessel imaging compared with conventional Doppler blood flow imaging, which is typically solely based on the temporal filtering on Doppler signal.

However, in vivo ultrasound data can be very complex due to the spatially varying tissue and noise characteristics, which compromise the performance of the eigen-based cluttering filtering operating on the full field-of-view (FOV) ultrasound data. To address this challenge, a block-wise SVD clutter filtering technique had been proposed, which divides the full FOV data into overlapped local blocks and processes each block of data separately. This block-wise local processing strategy enables better tissue clutter rejection on the basis of the local data statistics. However, a significant drawback of the block-wise SVD is the extremely computational cost due to the large amount of SVD calculations needed for the large spatially overlapping subsets of data, which limit the real-time implementation of the technique.

Another issue associated with block-wise SVD processing is the "grid pattern" artifacts resulting from the discontinuities between spatial blocks on the blood flow imaging, especially when the block overlap percentage is low, which may significantly deteriorate the appearance of blood flow image.

SUMMARY OF THE DISCLOSURE

The present disclosure addresses the aforementioned drawbacks by providing systems and methods for generating an image that depicts blood flow in a subject from ultrasound data acquired from the subject.

One general aspect of the present disclosure includes a method for estimating generating an image that depicts blood flow in a subject from ultrasound data acquired using an ultrasound imaging system. The method also includes accessing ultrasound data acquired from a subject with the ultrasound imaging system; generating a plurality of weighted ultrasound data sets, each weighted ultrasound data set being generated by applying a different weighting function to the ultrasound data, where each different weighting function applies a different spatial weighting to the ultrasound data; estimating blood flow signal data for each weighted ultrasound data set by tissue clutter filtering that weighted ultrasound data set; and generating a blood flow image from the estimated blood flow signal data, where the blood flow image depicts blood flow in the subject. Other embodiments of this aspect include corresponding computer systems, apparatus, and computer programs recorded on one or more computer storage devices, each configured to perform the actions of the methods.

Another general aspect of the present disclosure includes a method for generating an image that depicts blood flow in a subject from ultrasound data acquired using an ultrasound imaging system. The method also includes accessing ultrasound data acquired from a subject with the ultrasound imaging system; estimating blood flow signal data from the ultrasound data by clutter filtering tissue signals from the ultrasound data using a soft thresholding one of eigenvalues or singular values of the ultrasound data, where the soft thresholding includes applying a weighting function to the one of eigenvalues or singular value of the ultrasound data; and generating a blood flow image from the estimated blood flow signal data, where the blood flow image depicts blood flow in the subject. Other embodiments of this aspect include corresponding computer systems, apparatus, and computer programs recorded on one or more computer storage devices, each configured to perform the actions of the methods.

Still another general aspect of the present disclosure includes a method for generating an image that depicts blood flow in a subject from ultrasound data acquired using an ultrasound imaging system. The method also includes accessing ultrasound data acquired from a subject with the ultrasound imaging system; estimating blood flow signal data from the ultrasound data by clutter filtering tissue signals from the ultrasound data using a hard thresholding one of eigenvalues or singular values of the ultrasound data, where the hard thresholding includes applying a threshold that is adaptively determined based on minimizing a correlation between tissue clutter signals and blood flow signals in the ultrasound data; and generating a blood flow image from the estimated blood flow signal data, where the blood flow image depicts blood flow in the subject. Other embodiments of this aspect include corresponding computer systems, apparatus, and computer programs recorded on one or more computer storage devices, each configured to perform the actions of the methods.

In yet another general aspect of the present disclosure, a method for generating an image that depicts blood flow in a subject from ultrasound data acquired using an ultrasound imaging system is provided. The method also includes accessing ultrasound data acquired from a subject with the ultrasound imaging system; estimating blood flow signal data from the ultrasound data by clutter filtering tissue signals from the ultrasound data using a hard thresholding one of eigenvalues or singular values of the ultrasound data, where the hard thresholding includes applying a threshold that is adaptively determined based on a median of the one of eigenvalues or singular values of the ultrasound data; and generating a blood flow image from the estimated blood flow signal data, where the blood flow image depicts blood flow in the subject. Other embodiments of this aspect include corresponding computer systems, apparatus, and computer programs recorded on one or more computer storage devices, each configured to perform the actions of the methods.

As another general aspect of the present disclosure, a method for generating an image that depicts blood flow in a subject from ultrasound data acquired using an ultrasound imaging system. The method also includes accessing ultrasound data acquired from a subject with the ultrasound imaging system; estimating blood flow signal data from the ultrasound data by clutter filtering tissue signals from the ultrasound data using a hard thresholding one of eigenvalues or singular values of the ultrasound data, where the hard thresholding includes applying a threshold that is adaptively determined based on maximizing a curvature of a curve of the one of eigenvalues or singular values of the ultrasound data; and generating a blood flow image from the estimated blood flow signal data, where the blood flow image depicts blood flow in the subject. Other embodiments of this aspect include corresponding computer systems, apparatus, and computer programs recorded on one or more computer storage devices, each configured to perform the actions of the methods.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and methods for ultrasound clutter filtering to produce images of blood flow in a subject. The systems and methods described in the present disclosure may be advantageously applied to fast ultrasound imaging techniques, including ultrafast plane wave imaging techniques.

In some aspects, clutter filtering is implemented using hard thresholding techniques. In some other aspects, clutter filtering is implemented using soft thresholding techniques. In still other aspects, clutter filtering is implemented using the combination of spatially weighted data. As will also be described, in these and other instances, faster clutter filtering can be achieved by using eigenvalue decomposition.

In general, the clutter filtering can be based on a singular value implementation (e.g., a singular value decomposition ("SVD")), an eigenvalue implementation (e.g., an eigenvalue decomposition), or other similar mathematical framework. In one example, the clutter filtering can be implemented using a thresholding technique, which may be a hard thresholding or a soft thresholding. In still another example, clutter filtering can be implemented using a combination of spatially weighted data.

Thus, the systems and methods described here are capable of improving the operation of ultrasound imaging systems used for blood flow imaging. As one example, using the methods described in the present disclosure, the computational burden of clutter filtering can be reduced, thereby allowing the use of robust clutter filtering techniques to a wider range of ultrasound imaging system hardware. As another example, the reduced computational burden of the methods described in the present disclosure allow for faster processing of ultrasound data, which enables real-time clutter filtering and reconstruction of blood flow images with high frame rates.

Figure 1:
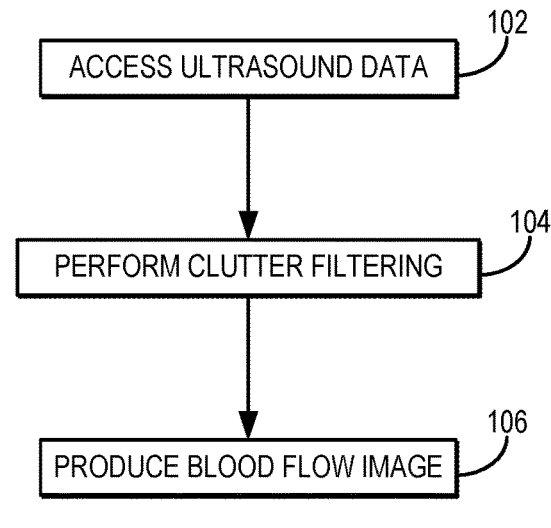
FIG. 1 is a flowchart setting forth the steps of an example method for generating a blood flow image from ultrasound data.

Referring now to FIG. 1, a flowchart is illustrated as setting forth the steps of an example method for producing an image depicting blood flow in a subject using an ultrasound system. The method includes accessing ultrasound data with a computer system, as indicated at step 102. Accessing the ultrasound data can include retrieving previously acquired ultrasound data from a memory or other suitable data storage device or medium. As another example, accessing the ultrasound data can include acquiring ultrasound data with an ultrasound system and communicating or otherwise transferring the ultrasound data to the computer system, which may be a part of the ultrasound system. The acquired ultrasound data can have any suitable form, and in one example may be ultrasound radio frequency ("RF")

signal data. In another example, the ultrasound data may be in-phase quadrature ("IQ") signal data. The ultrasound data can also be of other forms of ultrasound data, such as ultrasound data that include information from a pulse-echo ultrasound data acquisition.

Figure 2:
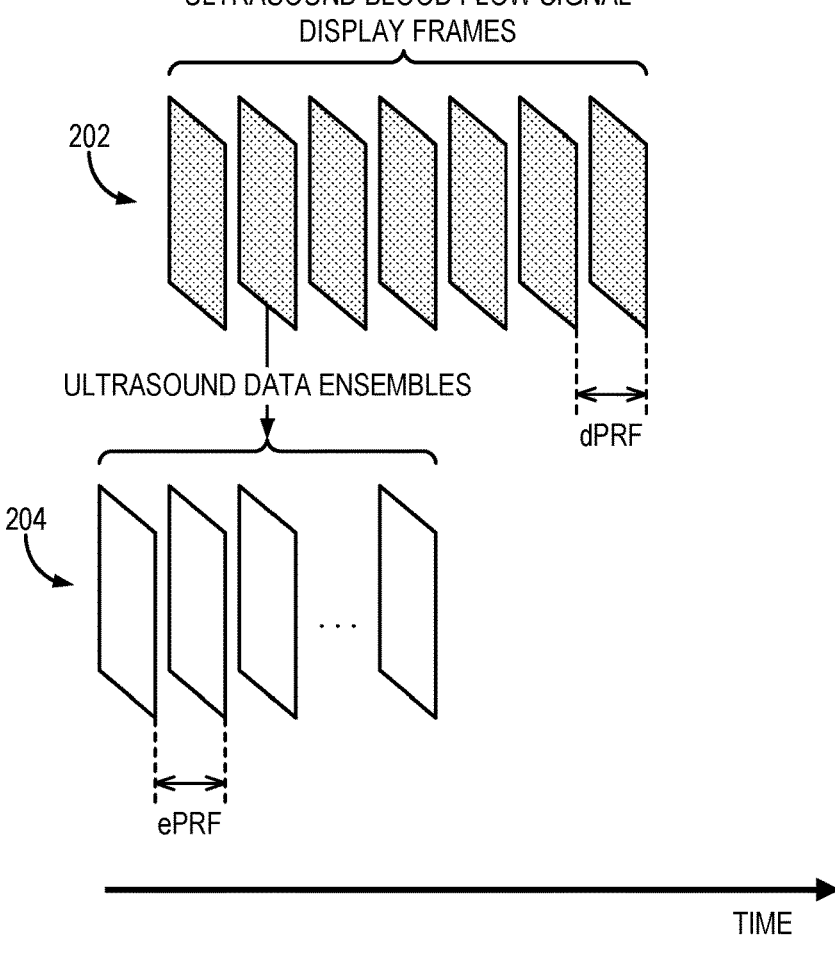
FIG. 2 depicts ultrasound blood flow signal display frames being generated from ultrasound data ensembles.

As one example, ultrasound data designated for blood flow imaging can be continuously acquired by the ultrasound system for real-time display, as shown in FIG. 2. In this example, the ultrasound blood flow signal display frames 202 are refreshed at a certain frame rate or pulse-repetition-frequency ("PRF") for continuous monitoring of the blood flow signal. Each ultrasound blood flow signal display frame is derived from multiple data ensembles 204 that are being collected at a higher frame rate or PRF (e.g., several hundreds to tens of thousands of ensembles per second) for blood flow signal processing. The ensemble PRF (or frame rate) can be referred to as "ePRF" and the display PRF (or frame rate) can be referred to as "dPRF."

The number of ensembles per ultrasound blood flow signal display frame depends on the desired dPRF of ultrasound blood flow imaging. Different ultrasound blood flow signal display frames can have mutually exclusive data ensembles, or can include the same ultrasound data ensembles (e.g., certain data ensembles are assigned to different consecutive frames in an overlapped sliding-window fashion) to fulfill a certain dPRF requirement. In general, the dPRF should be smaller or equal to ePRF.

The ultrasound data are processed using a clutter filtering technique, as indicated at step 104. In some instances, clutter filtering can implement high-sensitive localized spatial-temporal clutter filtering. As an example, such clutter filtering can implement applying different spatial weighting windows to the original ultrasound data separately, in order to generate multiple different weighted ultrasound data sets that can then be clutter filtered and combined. In some other instances, the clutter filtering implements fully adaptive and automatic spatial-temporal clutter filtering. As one example, such clutter filtering can implement hard thresholding based on a median singular value, eigenvalue, or other similar characteristic value. As another example, such fully adaptive clutter filtering can implement hard thresholding based on minimizing the correlation between blood signal and tissue signal. As still another example, such fully adaptive clutter filtering can implement soft thresholding by applying weightings to the singular value components, eigen-components, or other similar decomposed signal components. Examples of these techniques are described below in more detail.

As a result of the clutter filtering performed in step 104, blood flow signal data are estimated, from which an image of the blood flow in the subject can be reconstructed or otherwise produced, as indicated at step 106. The blood flow signal data can also be processed to suppress the tissue signal and noise, register the blood flow signals from different ultrasound data frames to suppress physiologic or operator-induced motion, and to calculate the desired blood flow signals such as color Doppler, power Doppler, spectral Doppler, vector Doppler, and so on.

Having described a general process for producing an image that depicts blood flow in a subject based on clutter filtered ultrasound data, methods for implementing high-sensitive localized spatial-temporal clutter filtering and/or fully adaptive and automatic spatial-temporal clutter filtering.

The present techniques apply to spatial-temporal ultrasound data acquired from high frame rate ultrasound imaging, including but not limited to plane wave imaging, with or without spatial compounding; diverging wave imaging, with or without spatial compounding; focused-beam ultrasound imaging; synthetic aperture imaging; any form of harmonic imaging or subharmonic imaging; or the combination of different imaging methods. Assume the original ultrasound data matrix, S, has a dimension of x×y×t, where x and y correspond to lateral and axial dimensions, respectively, and t represents the temporal dimension. Before spatial-temporal clutter filtering, the ultrasound matrix, S, is typically reshaped as a Casorati matrix, with a dimension of xy×t, where the columns of the Casorati matrix are vectorized frames. When the ultrasound data is 3D volume data, then the Casorati matrix will have dimension xyz×t where z represents the third spatial dimension (typically elevational dimension).

For singular value decomposition ("SVD") based clutter filtering methods, the SVD of the reshaped Casorati matrix, C, can be calculated as:

$$C = UDV^T \tag{1};$$

where the U is an orthonormal matrix whose columns are the left singular vectors of C, as expressed as $U=[u_1, u_2, \ldots, u_N]$; V is the orthonormal matrix whose columns are the right singular vectors, as expressed as $V=[v_1, v_2, \ldots, v_N]$; and D is a diagonal matrix whose diagonal entries are the singular values of C, which can be expressed by $D=\text{diag}(\sigma_1, \sigma_2, \ldots, \sigma_N)$, with singular values sorted in descending order. Here, N is the number of frames used for processing (i.e., temporal dimension), and can also be referred to as the ensemble or packet size in Doppler blood flow imaging. When performing the SVD of ultrasound spatial-temporal data, tissue clutter signal is typically represented by the low-order large singular values, while blood signal is typically represented by middle-to-high-order singular values. Therefore, after a singular value thresholding ("SVT") process (i.e., removing the lower-order singular values corresponding to tissue clutters), the filtered blood flow signal can be obtained as:

$$\hat{C} = SVT(C) = U\hat{D}V^T \tag{2};$$

where $\hat{D}$ is the diagonal matrix with the first $k^{th}$ singular values setting to zeros, $\hat{D}=\text{diag}(0, \ldots, 0, \sigma_{k+1}, \ldots, \sigma_N)$. The number of singular values, k, to be removed is an important parameter for tissue clutter rejection performance, and several fully adaptive methods for selecting optimal k are described in more detail below.

For high frame rate ultrasound data, the number of rows in the Casorati matrix can typically be much larger than the number of columns. For example, for ultrasound spatial-temporal data with a dimension of 100×100×50, the number of rows of the reshaped Casorati matrix is 10,000, which is 200 times larger than the number of columns (i.e., 50). SVD calculations of such a "tall" Casorati matrix can be time consuming, which is a significant challenge for the real-time implementation of the spatial-temporal based tissue clutter filtering.

To address this challenge, an eigenvalue decomposition ("EVD") based method can be implemented to speed up spatial-temporal clutter filtering, especially for the "tall" Casorati matrix derived from high frame ultrasound data.

Figure 3:
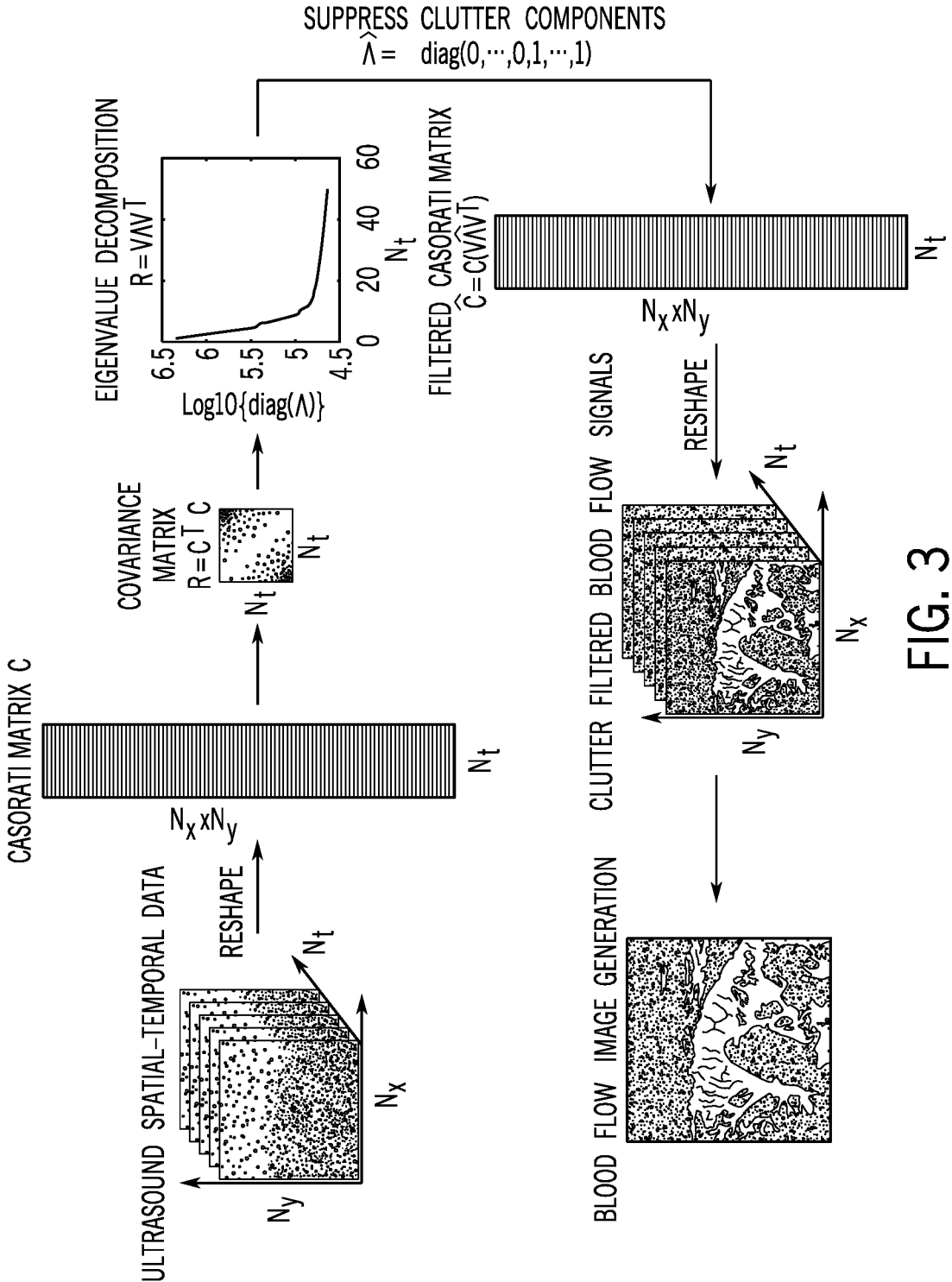
FIG. 3 shows a general workflow for an eigenvalue decomposition based tissue clutter filtering process.

FIG. 3 illustrates an example workflow setting forth the steps for an EVD-based method for tissue clutter filtering for blood flow imaging. In this example, a covariance matrix of the "tall" Casorati matrix of the ultrasound data can be derived, as follows:

$$R = C^T C = \sum_{i=1}^{xy}\left(s_i^T s_i\right); \qquad (3)$$

where s is the row vector of C (i.e., a data vector extracted from each spatial position with a size of 1×N, where N is the ensemble length). By calculating the EVD of the above covariance matrix, the eigenvalues and eigenvectors can be determined, as follows:

$$R = V\Lambda V^T \qquad (4);$$

where V is an N×N orthonormal matrix whose columns are the eigenvectors, which is identical to the right singular vectors from Eqn. (1), and can be expressed as $V=[v_1, v_2, \ldots, v_N]$; and $\Lambda$ is an N×N diagonal matrix $\Lambda=\mathrm{diag}(\lambda_1, \lambda_2, \ldots, \lambda_N)$ of the eigenvalues. The EVD calculation can be performed via any suitable algorithm, including but not limited to power method, orthogonal iteration method, QR iteration method, Lanczos/Arnoldi iterative method, Krylov subspace method, and so on. In some instances, it may not be necessary to calculate all of the eigenvalues and eigenvectors. Rather, in some instances the calculation of the first $k^{th}$ eigenvalues and the corresponding eigenvectors that are representing the tissue clutter can be sufficient for tissue clutter filtering. Reducing the number of eigen-components that are calculated facilitates further reducing the computational cost of tissue clutter filtering. Although the present disclosure describes methods for calculating all of the eigenvalues and eigenvectors, it is not a requirement.

The eigenvalues in $\Lambda$ are assumed to be sorted in descending order in magnitude. According to Eqn. (1):

$$C^T C=(UDV^T)^T UDV^T=V(D^T D)V^T \qquad (5);$$

hence, compared to Eqn. (4), the eigenvalues of R are the square of the corresponding singular values of C, i.e.

$$\lambda_i = \sigma_i^2.$$

Similar to SVD-based clutter filtering, then, when applying EVD to the spatial-temporal ultrasound data, tissue clutter is represented by the low-order large eigenvalues and blood flow signal is represented by the median to high-order smaller eigenvalues and the corresponding eigenvectors. By rejecting those eigenvalues and eigenvectors representing the tissue clutter, the blood flow signals can be recovered by a projection procedure, such as:

$$\hat{C}=C(V\Lambda V^T) \qquad (6);$$

where $\hat{C}$ is the obtained blood flow signal with tissue clutter suppressed, and $\check{\Lambda}$ is the diagonal matrix of the ones but rejecting the first $k^{th}$ diagonal entries by setting them to zeros, i.e., $\check{\Lambda}=\mathrm{diag}(0, \ldots, 0, 1, \ldots, 1)$. Several fully adaptive methods for selecting optimal number of eigenvalues and the corresponding eigenvectors (number of principal components, k) to be rejected are described below in more detail.

The matrix $\hat{C}$ is an xy×t Casorati matrix, $$\hat{C} = \begin{bmatrix} \hat{s}_1 \\ \vdots \\ \hat{s}_{xy} \end{bmatrix},$$

where $\hat{s}_i$ is the filtered blood flow signal at certain spatial position with a size of size of 1×N (here N=t). The Casorati matrix, $\hat{C}$, can then be reshaped back to the spatial-temporal format with a dimension of x×y×t, or blood flow signal $\hat{s}_i$ can be recovered pixel by pixel, as:

$$\hat{s}_i=s_i(V\Lambda V^T) \qquad (7).$$

Alternative to Eqn. (6), the principal components representing the tissue clutters can be first reconstructed and then subtracted from the original data to achieve tissue clutter filtering, as follows:

$$\hat{C}=C(I-V\Lambda V^T) \qquad (8);$$

where I is the identity matrix, and $\check{\Lambda}=\mathrm{diag}(1, \ldots, 1, 0, \ldots, 0)$, which preserves the first $k^{th}$ diagonal entries corresponding to the principal tissue clutter components and sets the remaining to zeros. Analogous to Eqn. (7), the blood flow signal at each spatial position can be recovered by:

$$\hat{s}_i=s_i(I-V\check{\Lambda}V^T) \qquad (9).$$

From the clutter filtered blood flow signals obtained above, different parameters to display as the output blood flow image can be calculated, including but not limited to the power of the blood flow signal (i.e., power Doppler image), velocity of the blood flow (can be display as color flow image), intensity of the blood flow signal (can be display as B-flow image), variance of the blood flow signal, etc. For example, the power Doppler image can be obtained as the mean or summation of the blood flow signal power along the temporal direction. For another example, the velocity of the blood flow can be obtained from the frequency shift of the Doppler blood flow signal (blood signal along the temporal direction) or from the phase of the lag-one autocorrelation of the Doppler blood flow signal.

The advantage of EVD-based clutter filtering methods on the "tall" ultrasound Casorati matrix is that it only needs to calculate the EVD of a small covariance matrix, R (the size of R can be determined by the ensemble size used for generating one blood flow image), while SVD is directly performed on the much larger Casorati matrix, C. Although the computational cost of EVD-based methods still includes the calculation of the covariance matrix (Eqn. (3)) and the calculation of blood flow signal via projection operation (Eqns. (6) or (8)), these matrix multiplication operations can be implemented easily in parallel by leveraging a multi-core CPU or a GPU in a very efficient manner. Therefore, EVD based filtering provides computation improvements over existing SVD-based clutter filtering techniques, especially for microvessel blood flow imaging based on high frame rate ultrasound, which involves processing a large number of "tall" matrices.

To implement eigen-based spatial-temporal clutter filtering in real-time, an adaptive and automatic selection of eigen-components (e.g., eigenvalues and the corresponding eigenvectors) representing the tissue clutter to be suppressed is provided by the methods described in the present disclosure. Typically, the ultrasound backscattering signal strength and the temporal behavior of the tissue components and the blood or noise components are different. More specifically, tissue typically has higher backscattering signal and moves more slowly in time. In contrast, blood has weaker backscattering signal and moves faster in time. Therefore, in eigen-based clutter filtering methods, such as EVD based filtering or the SVD based filtering, tissue signal is typically represented by the low-order singular values or eigenvalues with larger intensity/power and lower spatial-temporal coherence, while blood signal is represented by middle-to-small singular values or eigenvalues.

One common drawback of currently available methods for tissue clutter filtering is that they make use of hard thresholding (i.e., a threshold is identified, and all eigenvalues above which are set to be zeros and below which are preserved), which may compromise the tissue clutter filtering performance when tissue clutter and blood signals have large overlaps in eigen-components. Another drawback of currently available method is that they often make use of a predefined threshold (e.g., an eigenvalue intensity, a relative change of eigenvalue, a Doppler frequency) in order to enable adaptive thresholding, and the performance of tissue clutter suppression is largely dependent on that predefined threshold.

The systems and methods described in the present disclosure overcome these drawbacks by providing fully adaptive and automatic thresholding techniques for eigen-based clutter filtering. In one example, the optimal adaptive threshold can be identified as a function of median singular value or median eigenvalue. In another example, the optimal adaptive threshold can be identified by minimizing the spatial correlation between the reconstructed tissue clutter signal and blood flow signal. In still another example, a soft thresholding strategy is used instead of hard thresholding. In these latter instances, a weighting function is applied to the singular values or eigenvalues in order to adaptively achieve the suppression of tissue clutters. In still another example, the optimal adaptive threshold can be identified by maximizing the curvature of the singular value curve or eigenvalue curve. These methods are described in more detail below.

According to the low rank approximation, an optimal threshold may be a simple relationship to the median empirical singular value. In general, the threshold can be expressed as a function of the median singular value or median eigenvalue:

$$\text{Threshold} = f(\sigma_{median}) \tag{10}.$$

The eigen-components with singular values larger than this threshold can be considered as tissue clutter and can be removed for tissue clutter filtering. In one example, the threshold can be proportional to the median singular value, as:

$$\text{Threshold} = b \cdot \sigma_{median} \tag{11};$$

where b is an arbitrary scaling factor. As one non-limiting example, the value of b can be b=1.5. Once the threshold is identified, the singular values larger than the threshold can be removed (e.g., by setting to be zeros), and the blood flow signal can be reconstructed as described above. The coefficient can be varying when the matrix dimension is changing. A singular value threshold based on Eqns. (10) or (11) can be converted to thresholds of eigenvalues, given that the eigenvalue equals to the square of the singular values, $$\lambda_i = \sigma_i^2.$$

The scaling factor, b, can be different for different targeted media or tissues (e.g., kidney, liver, thyroid) and different imaging settings (e.g., different frame rate PRF) and different ultrasound transducers. A look-up table of scaling factors can also be established for different imaging settings and ultrasound transducers for different targeted tissues, which can enable real-time implementations. A user interface can also be generated and provided to a user, such that the user can adjust the scaling factor in real-time to achieve a better tissue suppression performance for specific applications.

As another example, hard thresholding for clutter filtering can be performed on the basis that the optimal threshold for the reconstructed blood flow signal and tissue clutter should have the most different spatial patterns. For instance, assuming the first $k^{th}$ largest eigenvalues are corresponding to the tissue clutter, the tissue clutter and blood flow signal can be reconstructed according to Eqn. (6) separately:

$$\hat{C}_T = C(V\hat{\Lambda}_T V^{\,T}) \tag{12};$$

$$\hat{C}_B = C(V\hat{\Lambda}_B V^{T}) \tag{13};$$

where $\hat{C}_T$ is the reconstructed tissue clutter signal; $\hat{C}_B$ is the reconstructed blood flow signal; $\hat{\Lambda}_T = \text{diag}(1, \ldots, 1, 0, \ldots, 0)$ is the diagonal matrix of ones, which keeps the first $k^{th}$ diagonal entries that are representing tissue clutters; and $\hat{\Lambda} = \text{diag}(0, \ldots, 0, 1, \ldots, 1)$ is the diagonal matrix of ones, but setting the first $k^{th}$ diagonal entries to be zeros.

Based on the assumption that an optimal k (i.e., the number of eigen-components or low ranks to be rejected) will result in the blood flow signal and tissue clutter being best separated, and thus $\hat{C}_T$ and $\hat{C}_B$ have the most different spatial patterns: the blood flow image from $\hat{C}_B$ reveals the vasculature structure, while the tissue clutter image from $\hat{C}_T$ represents the tissue morphology contaminated with ultrasound speckles.

This spatial pattern difference, or similarity, between tissue image and blood flow image can be quantitatively evaluated by a variety of indices, including but not limited to cross-correlation coefficient, normalized cross-correlation coefficient, absolute amplitude difference, relative difference, and so on. In the case of using normalized cross-correlation coefficient as the quantitative evaluation index, the problem can be modeled as finding a value for k where the tissue clutter image and the blood flow image have a minimized normalized cross-correlation coefficient:

$$\min_{1 \le k \le N} \{N_{corr}(k)\}; \tag{14}$$

where $N_{corr}(k)$ can be expressed as a function of k, as follows:

$$N_{corr}(k) = \frac{\sum I_T(k) \cdot I_B(k)}{\sqrt{\sum I_T(k)^2} \cdot \sqrt{\sum I_B(k)^2}}; \tag{15}$$

where k is the number of eigen-components identified as tissue clutter, and k can be 1 to N (i.e., the ensemble size); and $I_T(k)$ and $I_B(k)$ are the tissue and blood flow images obtained from $\hat{C}_T$ and $\hat{C}_B$, respectively, at a given k. For example, $I_T(k)$ and $I_B(k)$ can be the power image of $\hat{C}_T$ and $\hat{C}_B$, respectively. For another example, $I_T(k)$ and $I_B(k)$ can be the mean intensity image of $\hat{C}_T$ and $\hat{C}_B$, respectively.

Calculating Eqns. (12) and (13) at every k can involve a large computational cost. In these instances, the left singular matrix, U, can be leveraged to reduce this computational burden. As noted in Eqn. (1), the columns of U are the left singular vectors that provide the spatial information of each eigen component. This left singular matrix can be expressed as:

$$U = [U_1, U_2, \ldots, U_N] \tag{16};$$

11 where $u_i$ is the $xy\times1$ left singular vector or spatial singular vector corresponding the $i^{th}$ eigen-component. For a given k, the tissue image $I_T(k)$ can be obtained from the first $k^{th}$ left singular vectors (e.g., from $u_1$ to $u_k$), and the blood flow image $I_B(k)$ can be obtained from the rest of the left singular vectors (e.g., from $u_{k+1}$ to $U_N$). In general, the tissue image $I_T(k)$ and the blood flow image $I_B(k)$ can be $$I_T(k) = \sum_{i=1}^{k} w_i|u_i|; \tag{17}$$

$$I_B(k) = \sum_{i=k+1}^{N} w_i|u_i|; \tag{18}$$

where $|u_i|$ indicates the magnitude of $u_i$; and $w_i$ is a weight applied to each spatial singular vector. The weight, $w_i$, can have an arbitrary value. In one non-limiting example, $w_i$ can be equal to the singular values (i.e., $w_i=\sigma_i$). Note that $I_B(k)$ and $I_T(k)$ are vectorized images with a dimension of $xy\times1$, which can be reshaped back to the $x\times y$ 2D spatial image. By minimizing the correlation between $I_B(k)$ and $I_T(k)$ based on Eqns. (14) and (15), an optimal value for k that best separates the tissue clutter and blood flow signal can be computed.

In one example, if $w_i=1$, the tissue image $I_T(k)$ and the blood flow image $I_B(k)$ can be calculated as:

$$I_T(k) = \sum_{i=1}^{k} |u_i|; \tag{19}$$

$$I_B(k) = \sum_{i=k+1}^{N} |u_i|. \tag{20}$$

Note that the number of spatial singular vectors used to generate $I_B(k)$ and $I_T(k)$ are different according to Eqns. (17) and (18). Thus, the following variants of calculating $I_B(k)$ and $I_T(k)$ can also be adopted to balance the number of spatial singular vectors used. In one example, the tissue image $I_T(k)$ and the blood flow image $I_B(k)$ can be calculated as:

$$I_T(k) = \sum_{i=1}^{k} w_i|u_i|; \tag{21}$$

$$I_B(k) = \sum_{i=k+1}^{2k} w_i|u_i|. \tag{22}$$

Figure 5:
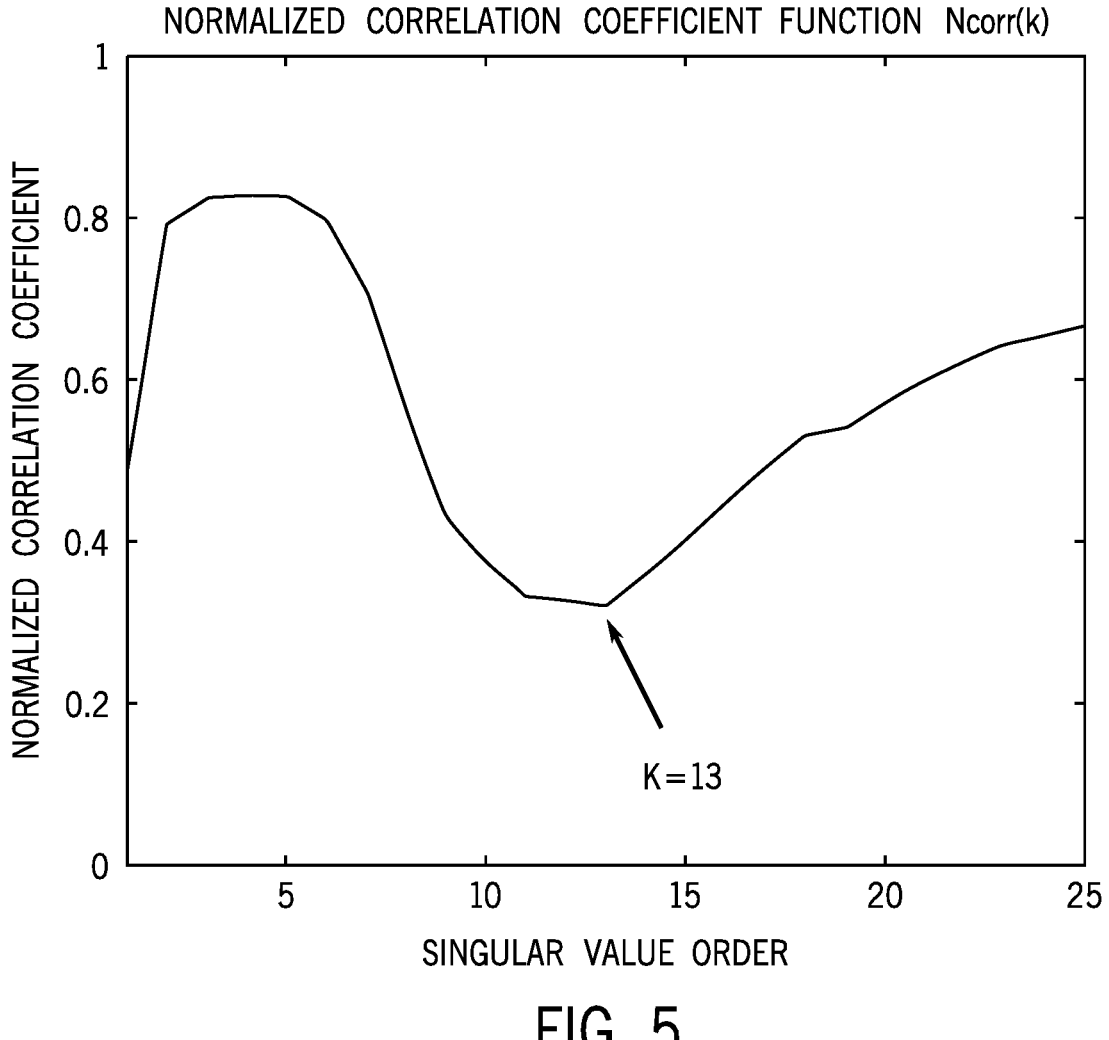
FIG. 5 shows an example of a normalized correlation coefficient function that can be used for hard thresholding clutter filtering.

An example of $N_{corr}(k)$ as a function of k based on Eqns. (15), (21), and (22) is shown in FIG. 5. The optimal k is identified as 13 at the minimum correlation coefficient, where the $I_T(k)$ and $I_B(k)$ are most distinct.

In another example, the tissue image $I_T(k)$ and the blood flow image $I_B(k)$ can be calculated as:

$$I_T(k) = \sum_{i=1}^{k} w_i|u_i|; \tag{23}$$

$$I_B(k) = \sum_{i=k+1}^{k+f_n} w_i|u_i|; \tag{24}$$

12 where $f_n$ is an arbitrary number indicating the number of singular vectors used to calculate the blood flow image, $I_B(k)$, like $f_n=20$.

In still another example, the tissue image $I_T(k)$ and the blood flow image $I_B(k)$ can be calculated as:

$$I_T(k) = \sum_{i=k-f_n+1}^{k} w_i|u_i|; \tag{25}$$

$$I_B(k) = \sum_{i=k+1}^{k+f_n} w_i|u_i|. \tag{26}$$

In this case the numbers of singular vectors used for calculating $I_T(k)$ and $I_B(k)$ are equaled, both are $f_n$. The tissue image $I_T(k)$ and the blood flow image $I_B(k)$ are calculated as a summation of the absolute value of the spatial singular vectors (from Eqns. (17)-(26)); however, this is not a requirement. In other examples, the $I_T(k)$ and $I_B(k)$ can be calculated using other suitable forms, including but not limited to the summation of spatial singular vectors, the summation of the power of spatial singular vectors, and so on.

For the EVD-based tissue clutter filtering method described above, only eigenvalues and right eigenvectors V are calculated. However, according to Eqn. (1):

$$CV=UD \tag{27};$$

which can also be expressed as:

$$Cv_i=\sigma_i u_i \tag{28}.$$

Given that the eigenvalues are the square of singular values $$\left(\text{i.e., } \lambda_i = \sigma_i^2\right),$$

the spatial eigenvectors, $u_i$, can thus been calculated. After the optimal number of tissue eigen-components, k, is identified, the blood flow signal can be obtained (e.g., via Eqn. (6)) as described above.

For most of the cases, the number of eigen-components representing tissue clutter is limited, and thus it may not be necessary to calculate the correlation coefficient of all the possible k. For example, only half of the possible k and the corresponding $u_i$ may be sufficient for finding out the minimum correlation coefficient, and thus sufficient to find out the number of tissue eigen-components to be suppressed. This approach can reduce the computational time for real-time calculations. Again, there can be a user interface that the operator can fine adjust the k in real-time to achieve a better tissue suppression performance for specific applications. In the above equations, the correlation was calculated between tissue image $I_T(k)$ and blood flow image $I_B(k)$, however, this is not a requirement. As another example, the correlation can also be calculated between $I_T(k)$ and $I_B(k+j)$, where j is an integer, and the number of eigen-components to be removed can be identified as either k or k+j, or a linear combination of k and k+j.

There is often a sharp transition in the singular value curve or eigenvalue curve (i.e., the curve of singular values or eigenvalues sorted in descending order), which relates to the transition of the tissue components to the blood components. At the transition location, the singular value curve or eigenvalue curve often will have the maximum local curvature. Assuming the first $k^{th}$ largest singular values or eigenvalues correspond to the tissue clutter, the optimal k can be related to finding the maximum curvature of the singular value curve or eigenvalue curve.

As a non-limiting example, assuming the singular value curve or eigenvalue curve can be modeled as $y=f(k)$, the curvature of the curve can be estimated as:

$$\text{curvature} = \frac{|y''|}{\left(1 + y'^2\right)^{3/2}}; \tag{29}$$

where y' and y'' are the first and second derivatives of y, respectively.

Instead of direct estimation on the original singular value curve or eigenvalue curve, a linear or nonlinear scale can also be applied to the curve before calculating the curvature. In one example, a linear scale can be applied to the singular value or eigenvalue curve, such that $y=\alpha \cdot f(k)$, where the scaling factor, a, can be an arbitrary value. In another example, a nonlinear scale, such as logarithm of the curve, can be applied, such that $y=\log_{10}f(k)$. Any other suitable nonlinear scale or transformation can also be applied, after which the curvature of the curve can be calculated.

Figure 6A:
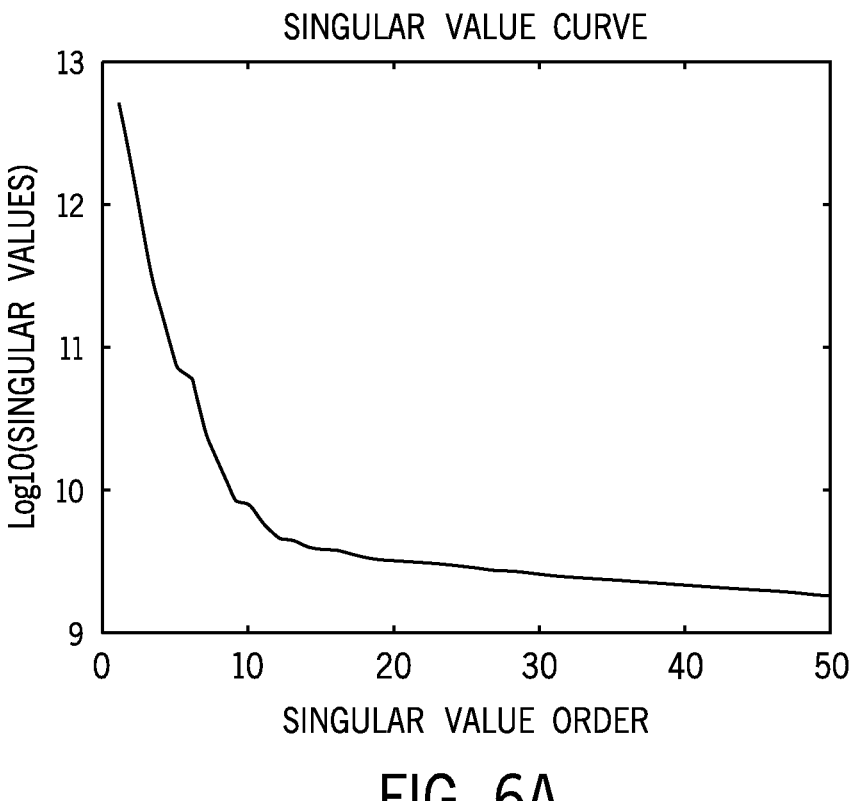
FIGS. 6A and 6B show an example singular value curve (FIG. 6A) and the corresponding curvature based on a nonlinear scaling (FIG. 6B).
Figure 6B:
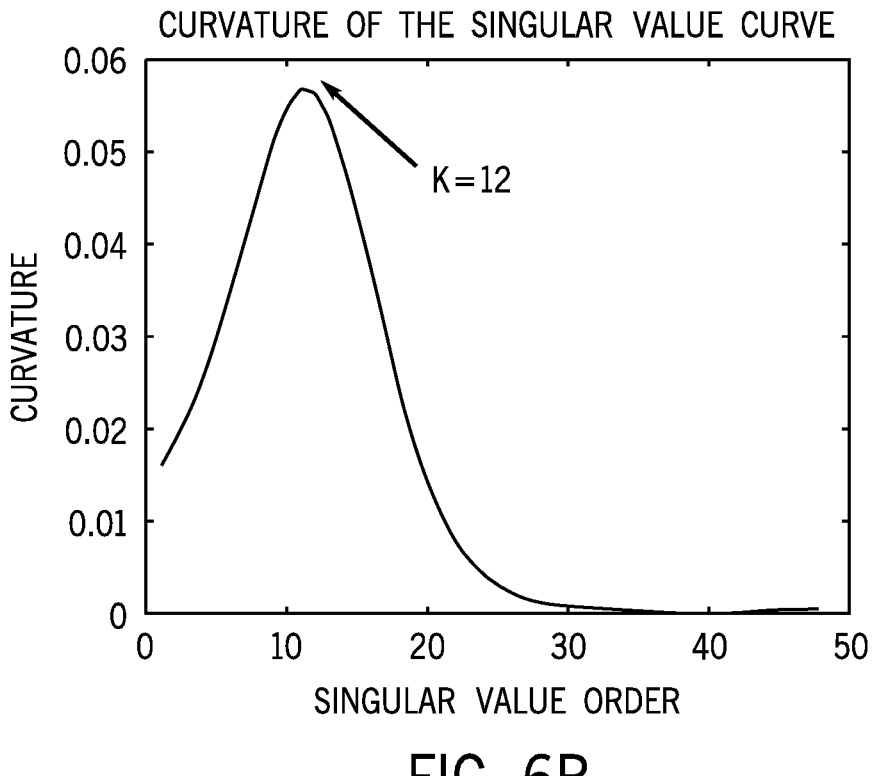

An example of the singular value curve and the corresponding curvature based on $y=\log_{10}f(k)$ is shown in FIGS. 6A and 6B, respectively. By localizing the maximum of the curvature, the number of low-ranks to be rejected can be determined. Since the curvature equals the reciprocal of the local radius of a curve, this method of finding the maximum curvature is similar to finding the minimum of radius of a curve.

The above methods are based on the hard thresholding that the singular values or eigenvalues above the threshold are set to be zeros. However, for most in vivo applications, especially where tissue motion is present, the tissue clutter and blood flow signal can have large overlap in terms of eigen-components. That is, the tissue eigen-components can include parts of blood flow signals, and vice versa.

It is an aspect of the present disclosure to provide a soft thresholding technique for adaptive clutter filtering by adding a weighting function to the singular values or eigenvalues, so as to achieve robust and adaptive tissue clutter suppression. The weightings applied to the eigen-components can be a function of either singular value (or eigenvalue) or Doppler frequency of the eigenvectors, or both. For instance, the tissue clutter components can be characterized by relatively larger eigenvalues or singular values, and relatively low Doppler frequency due to slow tissue motion. On the other hand, blood flow signals can be characterized by smaller eigenvalues or singular values, and relatively higher Doppler frequency due fast blood flow motion. More generally, the weights applied to the eigen-components can be expressed as a function of singular value (eigenvalue), spatial singular vector, and temporal singular vector:

$$wt_i=f(\sigma_i,u_i,v_i) \tag{30}$$

In general, the weighs, $wt_i$, can be directly applied to the singular values (eigenvalues) to achieve the soft thresholding. Instead of setting the first $k^{th}$ singular values to zeros (i.e., $\hat{D}=\text{diag}=(0, \ldots, 0, \sigma_{k+1}, \ldots, \sigma_N)$ or $\hat{\Lambda}=\text{diag}$ $(0, \ldots, 0, 1, \ldots, 1)$ here the weighted diagonal matrix for singular values can be:

$$\hat{D}=\text{diag}(wt_1 \cdot \sigma_1, wt_2 \cdot \sigma_2, \ldots, wt_N \cdot \sigma_N) \tag{31};$$

and the weighted diagonal matrix for EVD can be:

$$\hat{\Lambda}=\text{diag}(wt_1, wt_2, \ldots, wt_N) \tag{32}.$$

Then, the blood flow signal can be obtained via Eqns. (2) or (6).

Figures 7A, 7B, 7C:
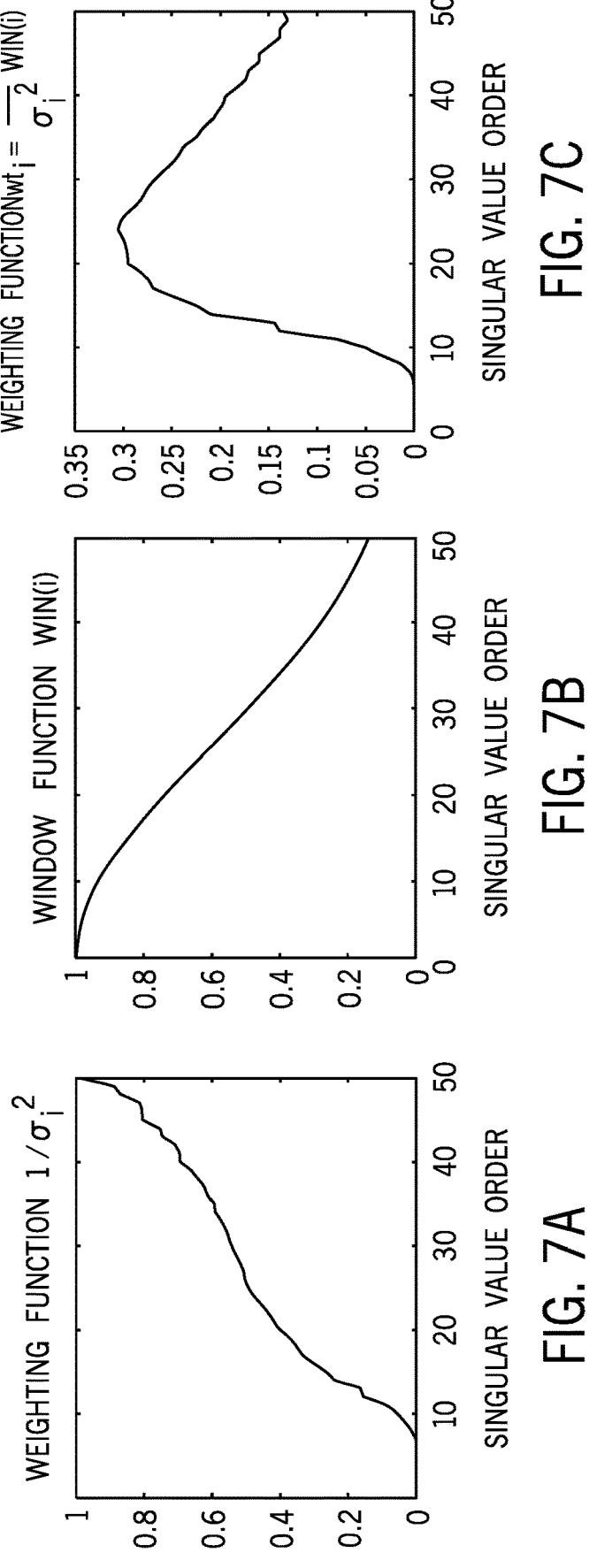
FIGS. 7A-7E show examples of weighting functions (FIGS. 7A-7C) and an example singular value curve before (FIG. 7D) and after (FIG. 7E) weighting.

Another practical design of weightings can be:

$$wt_i=f(\sigma_i) \tag{33};$$

where the weight is a function of the singular value. In general, the larger singular values (eigenvalues) represent the tissue components and can be reduced by a larger amount (designated by a smaller weights). In contrast, the smaller singular values (eigenvalues) correspond to the blood signals and can be reduced by a smaller amount (designated by larger weights). However, the function $f(\sigma_i)$ can be any suitable form that can achieve the tissue clutter suppression and blood flow signal enhancement, including but not limited to exponential functions, sigmoid functions, tangent functions, polynomial functions, and so on. As one non-limiting example, the weight can be calculated as:

$$wt_i = f(\sigma_i) = \frac{1}{\sigma_i^m}; \tag{34}$$

where m>0, which controls the order of the weighting function. As an example, for m=2 an example of $wt_i$ is plotted in FIG. 7A. Based on Eqn. (34), the value of the weight is inversely related to the singular value (i.e., the larger the singular value, the smaller the weight being applied to it), which can thus suppress the tissue components and enhance the blood flow components. However, when the singular value is very small (which can be the case for the noise and weak flow signals), $wt_i$ can be very large and thus the noise component may be enlarged and compromise the signal-to-noise ratio of the blood flow image. To compensate for these potential enhanced noise components, a window function can be applied to $wt_i$, such as, $$wt_i = \text{win}(i) \cdot \frac{1}{\sigma_i^m}; \tag{35}$$

where win(i) is the window function, which should have a smaller value at smaller singular value, $\sigma_i$, so that the noise components can be suppressed. For example, FIG. 7B shows an example of a window function, win(i), that is based on a Gaussian window. Any suitable form of window function can be utilized, including but not limited to Gaussian windows, triangular windows, Welch windows, sine windows, Hamming windows, and so on. To further avoid an unexpected enlargement of noise components, a threshold can also be set to remove extremely small $\sigma_i$ when calculating $wt_i$. As an example, $\sigma_i$ values smaller than the predefined $\sigma_{threshold}$ can be set as $\sigma_{threshold}$ when calculating the weighting function, $wt_i$.

Figures 7D, 7E:
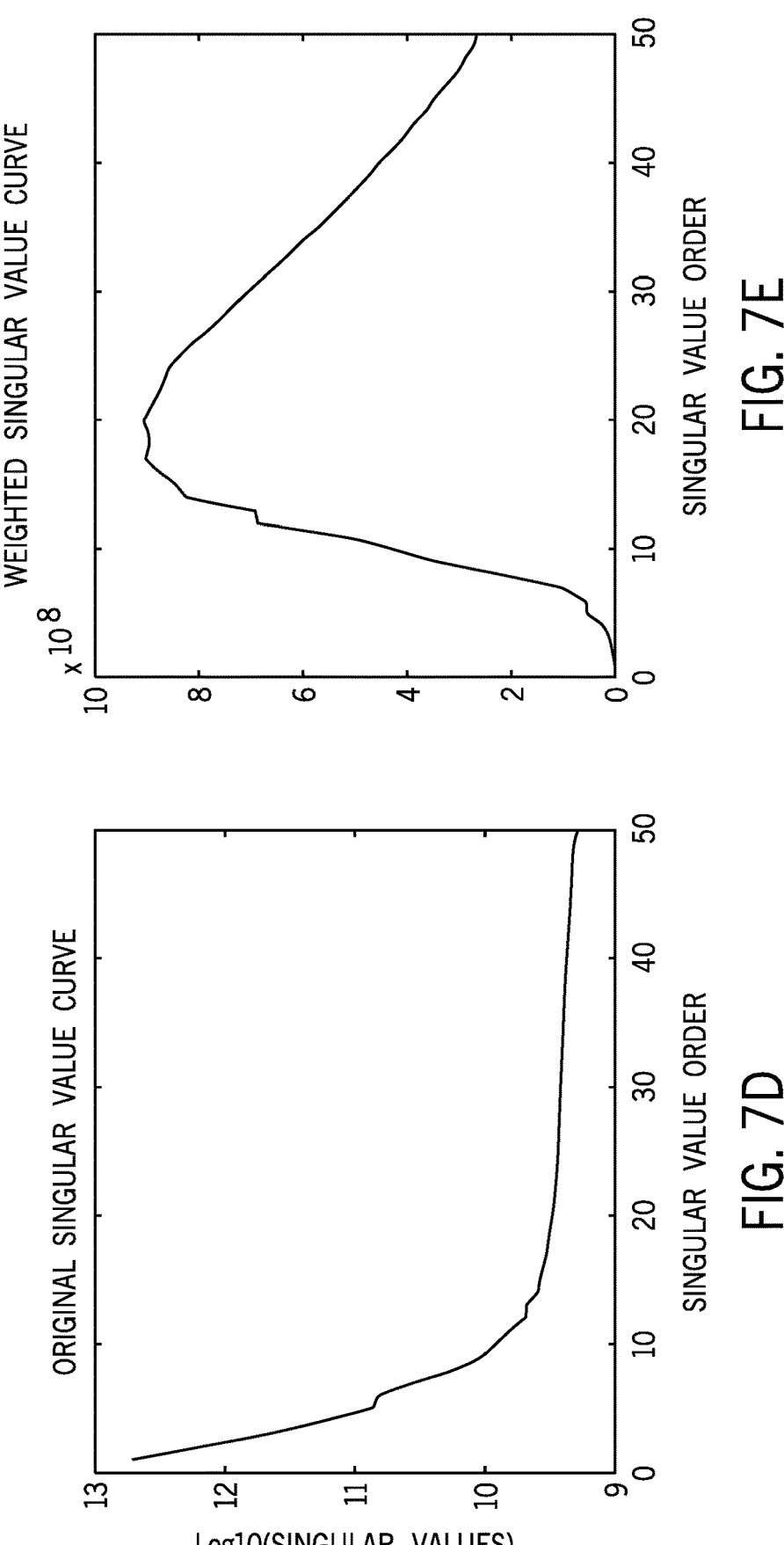

FIGS. 7A-7C show an example of weighting function $wt_i$ derived from patient data and based on Eqn. (35). The final weighting curve (FIG. 7C) is obtained by multiplying the curve in FIG. 7A by the window function in FIG. 7B. In FIG. 7D, the original singular value curve before filtering is shown, and the weighted singular value curve is shown in FIG. 7E, which is obtained by multiplying the original singular value curve by the weighting function $wt_i$ in FIG. 7C. The weighting function in FIG. 7C indicates the suppression of larger singular values (related to tissue clutter)

and very small singular values (related to noise), but enhances the median singular values (mainly related to blood flow signal).

Again, given that the eigenvalues are the square of singular value $$(\text{i.e., } \lambda_i = \sigma_i^2),$$

the weighting function based on eigenvalues and singular values can be convertible. Additionally, there can be a user interface that the operator can fine control of the weighting function to achieve a better tissue suppression performance for specific applications. As an example, the weighting function can be accessed and modified in the way similar to the time gain compensation ("TGC") control curve available on the ultrasound system used to acquire the ultrasound data.

Figures 8A, 8B, 8C:
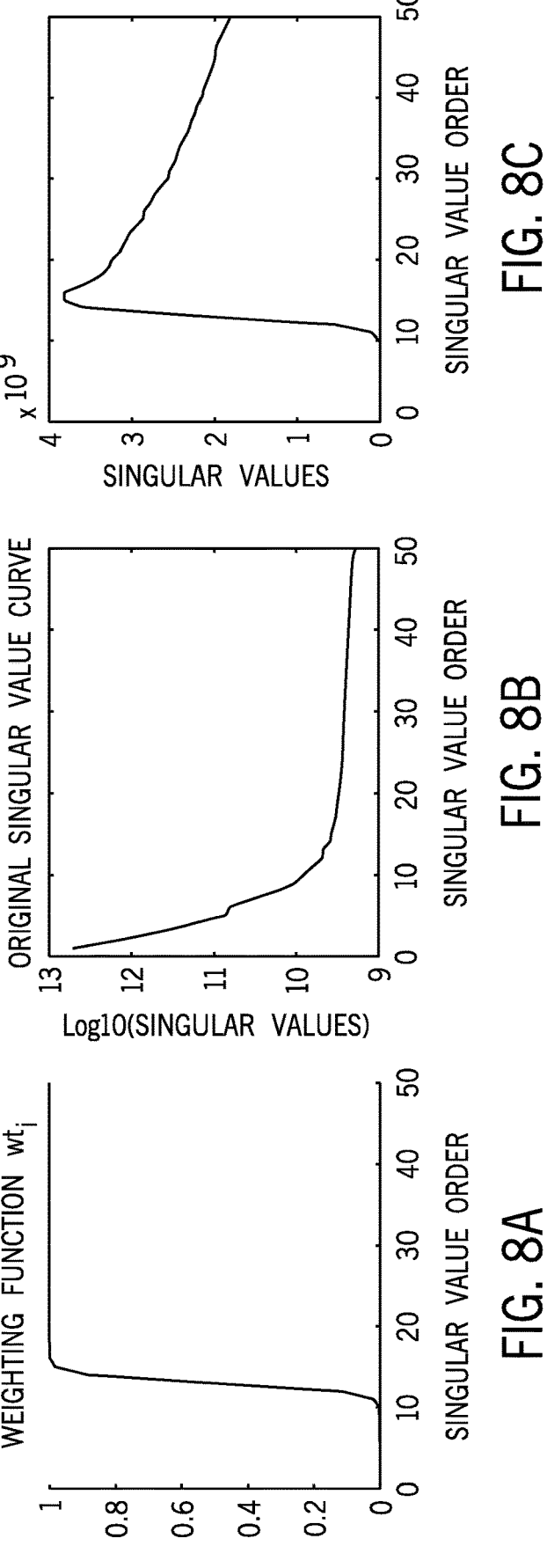
FIGS. 8A-8C show an example of a weighting function (FIG. 8A) applied to a singular value curve (FIG. 8B) to generate a weighted singular value curve (FIG. 8C).

The above methods to perform tissue clutter filtering, via either hard thresholding or soft thresholding, can be used separately or in combination with each other. Any combination between methods can be applied. For example, the threshold or the number of tissue eigen-components to be removed, k, obtained by one of the hard thresholding methods can be used to guide the design of weighting functions in a soft thresholding method. As an example, the number of tissue eigen-components, k, to be suppressed can be first identified with a hard thresholding technique, and then a sigmoid function can be generated centered at k as the weighting function in soft thresholding:

$$wt_i = \frac{1}{\left(1 + e^{-\alpha(i-k)}\right)}; \tag{36}$$

where $\alpha$ is an arbitrary scaling factor for the sigmoid function, for example $\alpha=2$, and k is the number of tissue eigen-components identified by the hard thresholding technique. An example of this weighting function is shown in FIG. 8A (here $\alpha=2$, k=13). The original singular value curve is shown in FIG. 8B for reference. The weighted singular value curve obtained by applying weighting function (FIG. 8A) to the original singular value curve (FIG. 8B) is shown in FIG. 8C.

For in vivo ultrasound data, the tissue, blood, and noise characteristics can be spatially varying, which compromises cluttering filtering performance when processing the full FOV ultrasound data. By conducting the clutter filtering based on localized ultrasound data, tissue clutter rejection can be better enabled according to local data statistics. Using a block-wise local processing technique for clutter filtering can suffer from an increased computational burden associated with the large amount of the overlapping block data, and can also lead to "grid-pattern" artifacts caused by sharp changes of blood flow energy between adjacent spatial blocks, especially when the block overlap percentage is low, which deteriorates the visualization of blood flow image.

It is an aspect of the present disclosure to provide a localized clutter filtering strategy that mitigates block artifacts issue and significantly reduces the number of data blocks. This framework can also be combined with the fast EVD based clutter filtering and robust adaptive thresholding methods described in the present disclosure to provide a high sensitive, localized processing based microvessel imaging can be implemented in real-time.

Figure 9:
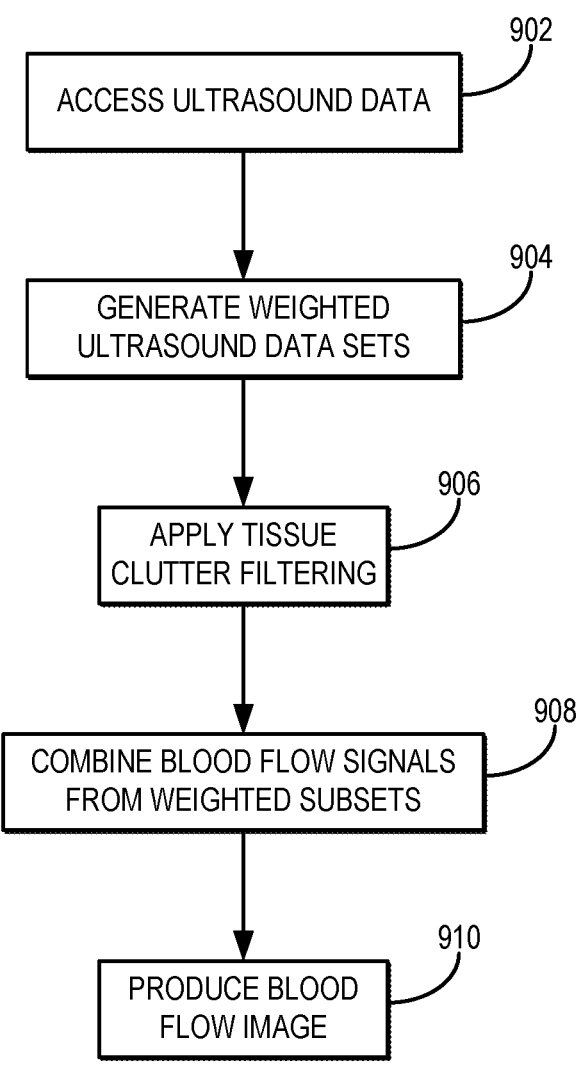
FIG. 9 is a flowchart setting forth the steps of an example method for generating a blood flow image from weighted ultrasound data sets to provide spatially and/or temporally localized tissue clutter filtering.

Referring now to FIG. 9, a flowchart is illustrated as setting forth the steps of an example method for clutter filtering ultrasound data using spatial weighting of the original ultrasound data to provide localized clutter filtering. The method includes accessing ultrasound data for processing, as indicated at step 902. As described above, accessing such data may include retrieving previously acquired data from a memory or other suitable data storage device or medium, or may also include acquiring the data in real-time.

Figure 4:
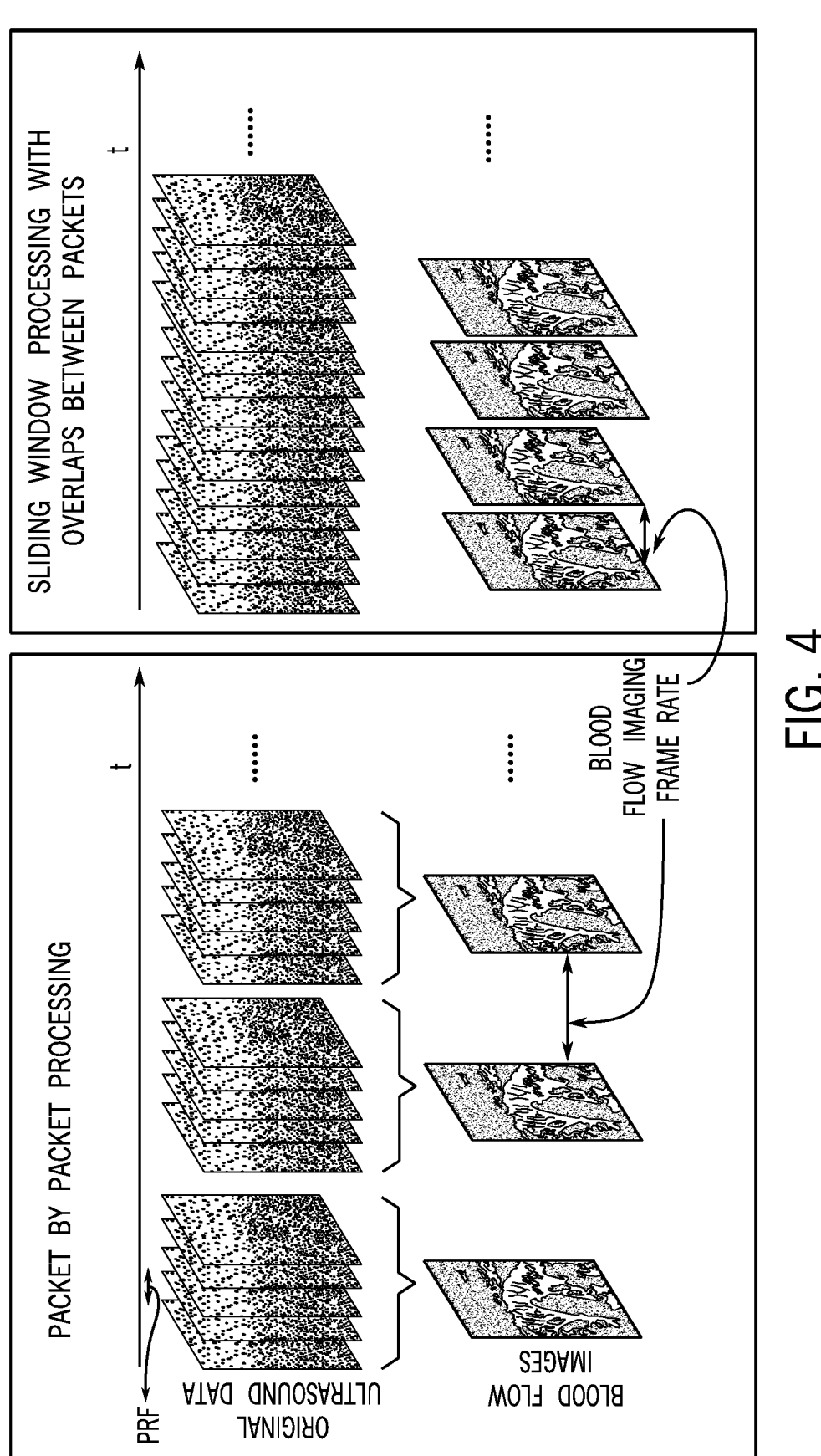
FIG. 4 shows examples of packet-by-packet processing of ultrasound data.

Rather than hard splitting the original data into overlapping spatial blocks, weighted data are generated by applying one or more weighting windows (e.g., 2D spatial weighting windows) to the original ultrasound data to generate multiple different weighted ultrasound data sets, as indicated at step 904. Any suitable 2D weighting windows can be applied to the original ultrasound data for the purpose of local processing, including but not limited to 2D Gaussian windows, 2D triangular windows, 2D Welch windows, 2D sine windows, 2D Hamming windows, and so on. FIG. 4 shows a set of four Gaussian windows centered at four different positions, as an example. Applying these four windows to the original ultrasound data separately will result in four different weighted ultrasound data sets. Assume C is an xy×t Casorati matrix reshaped from the original ultrasound data, as $$C = \begin{bmatrix} s_1 \\ \vdots \\ s_{xy} \end{bmatrix},$$

where $s_i$ is the ultrasound signal at a certain spatial position with a size of 1×N (here N is the ensemble size, N=t). The signal, $s_i$, can also be referred to as a slow-time ultrasound signal at a certain spatial pixel. Assume $$w = \begin{bmatrix} w_1 \\ \vdots \\ w_{xy} \end{bmatrix}$$

is the xy×1 Casorati matrix of the 2D weighting windows, with $w_i$ being the weight at the same spatial position of $s_i$. In this example, the Casorati matrix of the weighted ultrasound data can be expressed as:

$$C_w = WC = \begin{bmatrix} w_1 \cdot s_1 \\ \vdots \\ w_i \cdot s_i \\ \vdots \\ w_{xy} \cdot s_{xy} \end{bmatrix}; \tag{37}$$

Where W is a diagonal matrix of w (i.e., W=diag(w)). For each weighting window, the spatial positions around the window center typically have larger weights than the peripheral positions. Thus, the weighted ultrasound data typically represents the data information of the localized positions defined by the weighting windows where the ultrasound energy is dominant. For example, applying the 2D weighting window to the upper-left quadrant of the original data will generate a weighted ultrasound data set in which the energy in the upper-left quadrant will be dominant.

Each weighted ultrasound data set is then processed using tissue clutter filtering, as indicated at step 906. Any suitable tissue cluttering technique can be used, including but not limited to temporal high-pass filters, SVD-based filters, regression-based filters, EVD-based filters, those techniques described in the present disclosure, and so on.

As a non-limiting example, once the Casorati matrix $C_w$ of each weighted ultrasound data set is obtained, the SVD, EVD, or other suitable calculation can be performed for tissue clutter filtering. For EVD-based clutter filtering, a covariance matrix of the Casorati matrix $C_w$ can be first calculated, as follows:

$$R = C_w^T C_w = C^T W^T W C = \sum_{i=1}^{xy} w_i^2 (s_i^T s_i). \tag{38}$$

Based on the Eqn. (38), R can be considered as a weighted summation of $$s_i^T s_i,$$

where the weights here are the square of the weights applied to the original ultrasound data $$(\text{i.e., } w_i^2).$$

By calculating the EVD of R, the eigenvalues and eigenvectors can be obtained. Then, by suppressing the eigencomponents corresponding to the tissue clutter, the filtered blood flow signal can be reconstructed. As an example, the adaptive and automatic thresholding methods described in the present disclosure can be utilized to suppress the tissue clutter. The reconstructed blood flow signal can be expressed as:

$$\hat{C}_w = C_{aw}(V\hat{\Lambda}V^T) \tag{39};$$

or $$\hat{C}_w = C_{aw}(I - V\check{\Lambda}V^T) \tag{40};$$

Where $\hat{C}_w$ is the filtered blood flow signal with tissue clutter suppressed, and $\hat{\Lambda}$ and $\check{\Lambda}$ are diagonal matrices indicating the suppressing or preserving of the tissue eigencomponents, as detailed below. Here, $C_{aw}$ is the Casorati matrix of the original ultrasound data weighted by an arbitrary weighting window. Any suitable weighting window can be utilized here. In one example, $C_{aw}$ can be the input Casorati matrix $C_w$, such that $C_{aw} = C_w$. In another example, $C_{aw}$, can be the Casorati matrix of the original ultrasound data without weighting (or with weights=1), such that $C_{aw} = C$ The filtered blood flow signals generated from tissue clutter filtering the different weighted ultrasound data sets can then be combined to generate the combined blood flow signal, as indicated at step 908. The combined blood flow signals can be further processed to produce the blood flow image, as indicated at step 910.

For example, after the filtered blood flow signal $\hat{C}_w$ is obtained from each weighted ultrasound data set, the final blood flow signal can be combined from each separate blood flow signal. Any suitable combination method can be utilized to generate the final blood flow signal, including but not limited to summation, averaging, multiplication, and so on. In one example, the final blood flow signal can be generated by weighted summation of each separate blood flow signal, as:

$$\hat{C}_{final} = \sum_{i=1}^{N_d} \frac{1}{\beta_i} (\hat{C}_w)_i; \tag{41}$$

where the index i indicates the order of filtered blood flow signal; $N_d$ is the total number of blood flow signals used to generate the final blood flow signal; and $\beta_i$ is the weight applied to the $i^{th}$ blood flow signal before summation. The weight, $\beta_i$, can be an arbitrary value. In one example, all the weights, $\beta_i$, can be equal, such as $\beta_i = 1$. In another example, the weight $\beta_i$ applied to each blood flow signal can be dependent on the intensity, power, or velocity of the corresponding blood flow signal. For instance, the weight, $\beta_i$, can be the mean power of the blood flow signal, $(\hat{C}_w)$; in this case, the final blood flow signal is the summation of each separate blood flow signal normalized to its signal power.

Note that $\hat{C}_{final}$ is a Casorati matrix, which can be reshaped back to the spatial-temporal format with the same dimension as the original ultrasound data for imaging display. In Eqn. (41), the combination is performed on the Casorati matrix before reshaping back to the spatial-temporal format. However, the Casorati matrix of each separate blood flow signal can also be first reshaped back to the spatial-temporal format before summation. Then, the blood flow image can be produced on the basis of the final blood flow signal. However, the blood flow image can also be produced first for each separate blood flow signal, then all the blood flow images from different weighted ultrasound data are combined to produce the final blood flow image in a similar way as described above.

The produced blood flow image can be any suitable form, including but not limited to the power of the blood flow signal (i.e., power Doppler image), velocity of the blood flow (can be displayed as a color flow image), intensity of the blood flow signal (can be displayed as B-flow image), variance of the blood flow signal, and so on. It should be noted that the order of the steps shown in FIG. 9 can be appropriately adjusted. As one example, the blood flow image can be generated first for each filtered blood flow signal, and then all the blood flow images from different weighted ultrasound data can be combined to produce the final blood flow image.

In some implementations, before combination of the blood flow images from all the separate subsets of data, noise suppression can be applied to each separate blood flow image for SNR improvement. Any suitable noise suppression method can be applied here, including but not limited to noise equalization, noise subtraction, or noise reduction methods based on the correlation. In one example, the noise field can be experimentally measured by turning off the transducer transmission and only receiving with the same system configuration and imaging sequence (including same transducer, gain settings, transmit voltages, transmit pulse, receive filters, beamforming settings, etc.) as used for the actual blood flow signal acquisition. The noise suppressed blood flow image can be obtained with the estimated noise field subtracted from the original blood flow image. Note that for each separate data set, the noise field can be weighted by the same 2D spatial weighting window that is applied to the ultrasound data before subtraction.

For ultrasound systems in which the transducer transmission cannot be turned off, the ultrasound data can be acquired with the transducer transmitting into the air. For instance, a minimum transmission power without ultrasound gel can be set on the transducer surface. A clutter filter can be applied to the acquired ultrasound data to remove the strong echo reflection from the air, and the remaining data can be consider as noise, which can be used for noise subtraction or noise equalization for improvement of the blood flow imaging. Here, any suitable clutter filter can be applied, including but not limited to SVD based filters, EVD based filters, temporal filters, and so on.

Figure 10A:
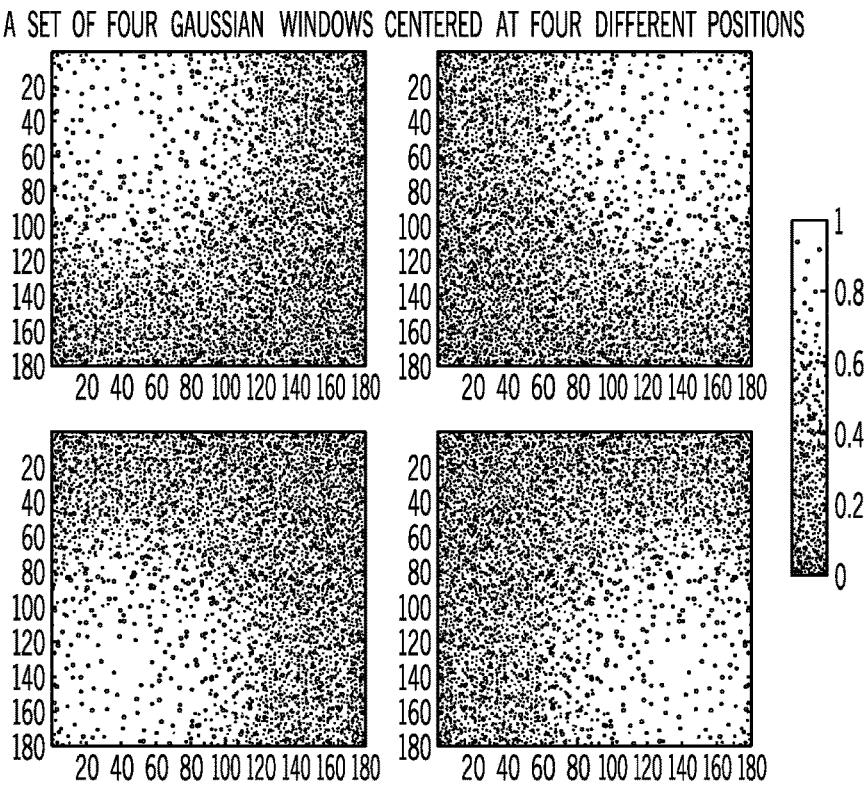
FIGS. 10A and 10B show examples of weighting functions that can be used to generate weighted ultrasound data sets.
Figure 10B:
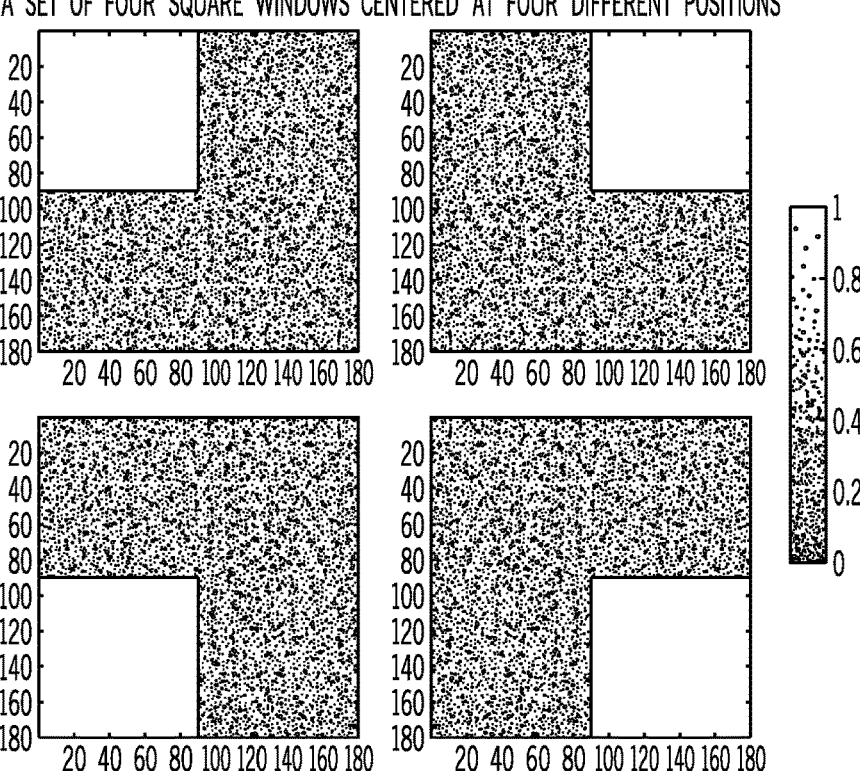

As an illustrative example, a set of four Gaussian windows is shown in FIG. 10A. As noted above, the number of windows, the position of the window center for each window, the shape of the windows, and the geometry of the windows can be arbitrary. In some instances, the windows can be at least partially spatially overlapping with each other. As another example, a set of four square windows, as shown in FIG. 10B, can also be utilized. Applying these windows to the original ultrasound data is equivalent to dividing the original ultrasound data into small blocks. A covariance matrix is formed can then be formed on the basis of each block data, such as by using Eqn. (38).

Further, the size of the weighting window does not need to be the same as the spatial dimension of the ultrasound data. For example, only the data with non-zero weight will be kept to form the covariance matrix for EVD calculation, which will reduce the data size and help speed up the calculation.

It can be advantageous for the weighting windows to have smooth transitions, such that an abrupt change of blood flow energy at the boundaries does not exist. This would largely mitigate block artifacts in the blood flow image. In these instances, a large number of weighted ultrasound data or a large overlap between weighting windows would not be needed, which can facilitate the real-time implementation of the technique.

Figure 11:
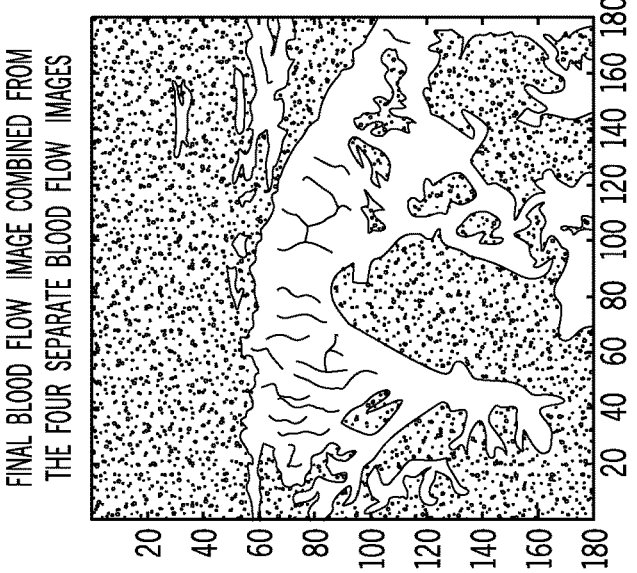
FIG. 11 shows an example of blood flow images obtained from weighted ultrasound data sets and their combination into a final blood flow image.

FIG. 11 shows an example of blood flow images obtained from weighted ultrasound data using the weighting windows in FIG. 10A. FIG. 11 also shows the final blood flow image combined from the four separate blood flow images.

For the sake of clarity, the methods described above have been described with respect to a 2D imaging context, but can also be applied to 3D, or even higher dimensional ultrasound blood flow imaging. For 3D blood flow imaging, for example, the weighting windows for localized processing can be in 3D format, including but not limited to 3D Gaussian windows, 3D triangular windows, 3D Welch windows, 3D sine windows, 3D Hamming windows, and so on. Similarly, the above method is described under EVD based clutter filtering context, but can also be applied to SVD based clutter filtering method or any other clutter filtering techniques.

For illustration, the methods described in the present disclosure have been described with respect to non-contrast blood flow imaging; however, they can be implemented in both contrast-enhanced and non-contrast ultrasound imaging. The ultrasound imaging used to acquire the ultrasound data can be any appropriate imaging strategy, including but not limited to plane wave imaging, with or without spatial compounding; diverging wave imaging, with or without spatial compounding; focused-beam ultrasound imaging; synthetic aperture imaging; any form of harmonic imaging or subharmonic imaging; or the combination of different imaging methods.

In conventional blood flow Doppler imaging, the ultrasound data are typically acquired and processed packet-by-packet. As a non-limiting example, a packet of ultrasound data, such as with a packet size (i.e., ensemble size, or the number of ultrasound frames used to perform clutter filtering) of 16 or so, is acquired and processed to generate a blood flow image. The systems and methods described in the present disclosure can process and display ultrasound data in a packet-by-packet manner, similar to the conventional Doppler imaging methods. The packet size for the techniques described in the present disclosure can be vary, and a larger packet size (e.g., 64 or higher) can be used for better tissue rejection and blood flow signal accumulation, while a smaller packet size can be advantageous when significant tissue motion is present.

Except for packet-by-packet acquisitions, high frame rate ultrasound data can be acquired continuously with a constant (or even non-constant) PRF or frame rate, and ultrasound data can be processed in a sliding window manner, such that the adjacent packets can have overlaps in the temporal direction, as shown in FIG. 4. For sliding window implementations, the packet size (e.g., the number of ultrasound frames used to perform clutter filtering) can be arbitrary, and the blood flow image can be displayed at a very high frame rate. Additionally, the blood flow signals after clutter filtering from different packets over long acquisition times can be accumulated to generate a blood flow image with higher SNR and higher sensitivity. Before accumulation, motion registration between blood flow images can be applied to compensate tissue motion when necessary to avoid blurring on the final blood flow image.

Figure 12:
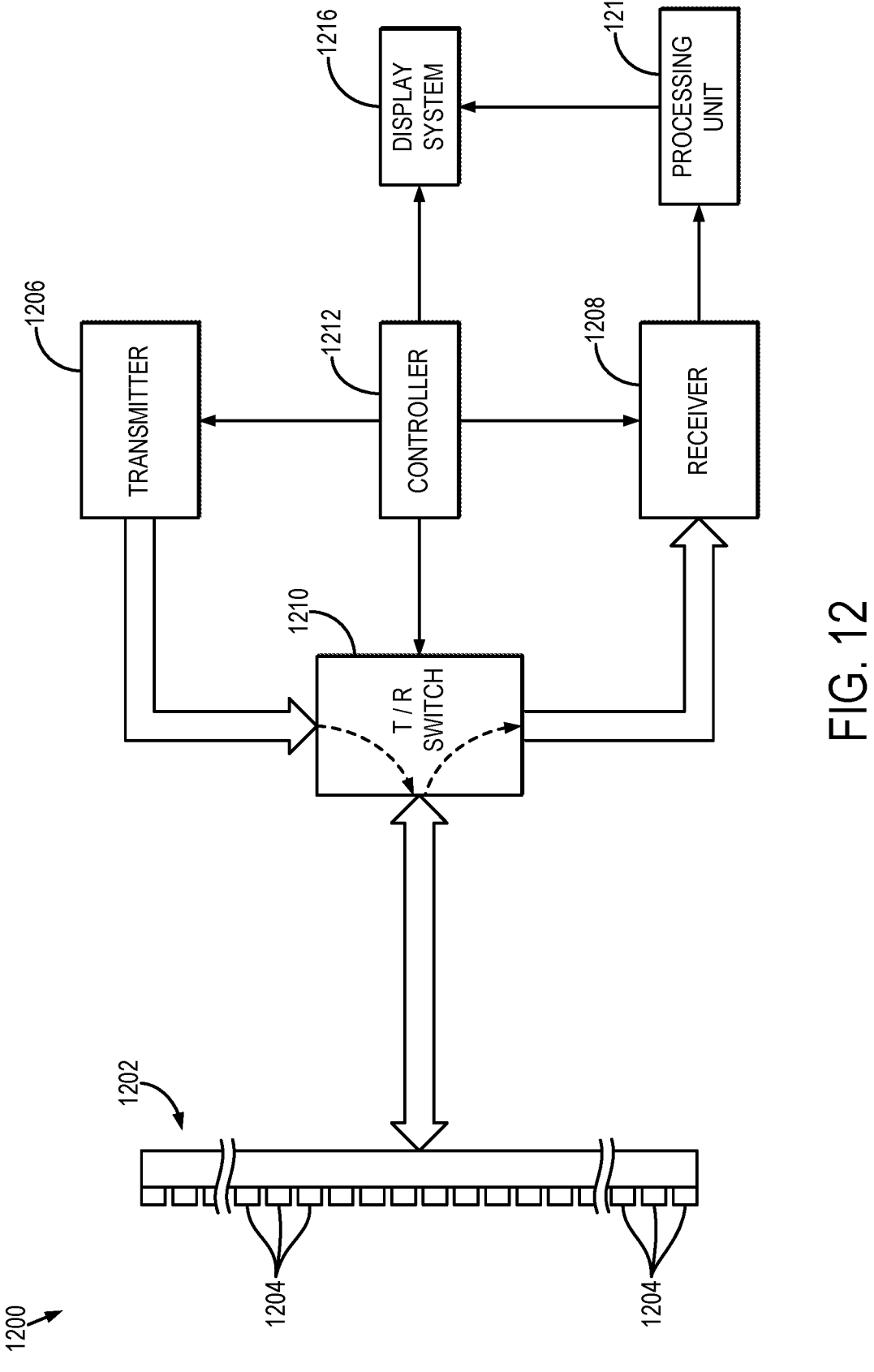
FIG. 12 is a block diagram of an example ultrasound system.

FIG. 12 illustrates an example of an ultrasound system 1200 that can implement the methods described in the present disclosure. The ultrasound system 1200 includes a transducer array 1202 that includes a plurality of separately driven transducer elements 1204. The transducer array 1202 can include any suitable ultrasound transducer array, including linear arrays, curved arrays, phased arrays, and so on. Similarly, the transducer array 1202 can include a 1D transducer, a 1.5D transducer, a 1.75D transducer, a 2D transducer, a 3D transducer, and so on.

When energized by a transmitter 1206, a given transducer element 1204 produces a burst of ultrasonic energy. The ultrasonic energy reflected back to the transducer array 1202 (e.g., an echo) from the object or subject under study is converted to an electrical signal (e.g., an echo signal) by each transducer element 1204 and can be applied separately to a receiver 1208 through a set of switches 1210. The transmitter 1206, receiver 1208, and switches 1210 are operated under the control of a controller 1212, which may include one or more processors. As one example, the controller 1212 can include a computer system.

The transmitter 1206 can be programmed to transmit unfocused or focused ultrasound waves. In some configurations, the transmitter 1206 can also be programmed to transmit diverged waves, spherical waves, cylindrical waves, plane waves, or combinations thereof. Furthermore, the transmitter 1206 can be programmed to transmit spatially or temporally encoded pulses.

The receiver 1208 can be programmed to implement a suitable detection sequence for the imaging task at hand. In some embodiments, the detection sequence can include one or more of line-by-line scanning, compounding plane wave imaging, synthetic aperture imaging, and compounding diverging beam imaging.

In some configurations, the transmitter 1206 and the receiver 1208 can be programmed to implement a high frame rate. For instance, a frame rate associated with an acquisition pulse repetition frequency ("PRF") of at least 100 Hz can be implemented. In some configurations, the ultrasound system 1200 can sample and store at least one hundred ensembles of echo signals in the temporal direction.

The controller 1212 can be programmed to design or implemented a stored imaging sequence. In some embodiments, the controller 1212 receives user inputs defining various factors used in the design of the imaging sequence.

A scan can be performed by setting the switches 1210 to their transmit position, thereby directing the transmitter 1206 to be turned on momentarily to energize transducer elements 1204 during a single transmission event according to the selected imaging sequence. The switches 1210 can then be set to their receive position and the subsequent echo signals produced by the transducer elements 1204 in response to one or more detected echoes are measured and applied to the receiver 1208. The separate echo signals from the transducer elements 1204 can be combined in the receiver 1208 to produce a single echo signal.

The echo signals are communicated to a processing unit 1214, which may be implemented by a hardware processor and memory, to process echo signals or images generated from echo signals. As an example, the processing unit 1214 can perform tissue clutter filtering and generate blood flow images using the methods described in the present disclosure. Images produced from the echo signals by the processing unit 1214 can be displayed on a display system 1216.

Figure 13:
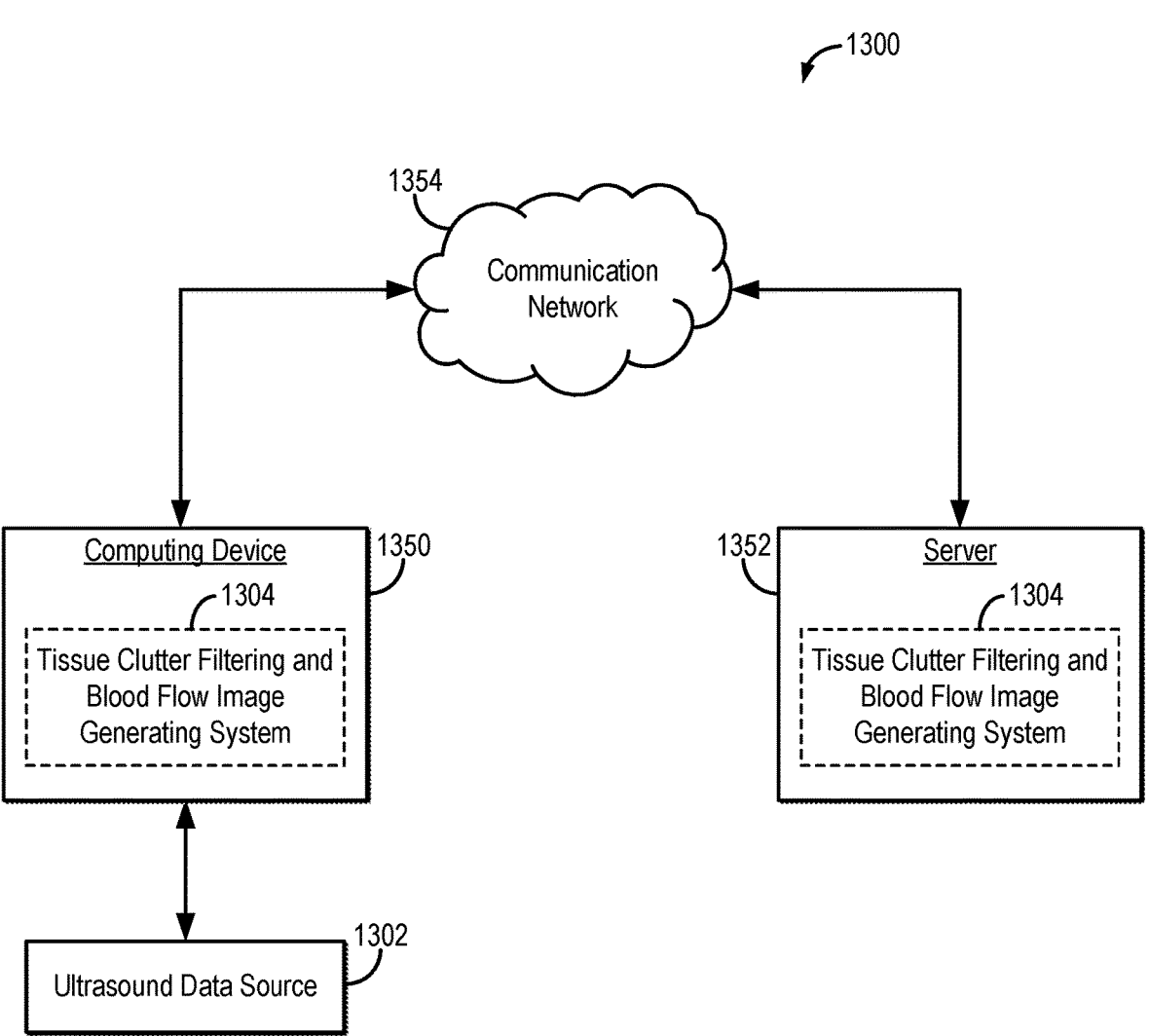
FIG. 13 is a block diagram of an example tissue clutter filtering and blood flow image generating system.

Referring now to FIG. 13, an example of a system 1300 for tissue clutter filtering and blood flow imaging in accordance with some embodiments of the systems and methods described in the present disclosure is shown. As shown in FIG. 13, a computing device 1350 can receive one or more types of data (e.g., ultrasound data) from ultrasound data source 1302, which may be an ultrasound data source. In some embodiments, computing device 1350 can execute at least a portion of a tissue clutter filtering and blood flow image generating system 1304 to generate blood flow images from data received from the ultrasound data source 1302.

Additionally or alternatively, in some embodiments, the computing device 1350 can communicate information about data received from the ultrasound data source 1302 to a server 1352 over a communication network 1354, which can execute at least a portion of the tissue clutter filtering and blood flow image generating system 1304. In such embodiments, the server 1352 can return information to the computing device 1350 (and/or any other suitable computing device) indicative of an output of the tissue clutter filtering and blood flow image generating system 1304.

In some embodiments, computing device 1350 and/or server 1352 can be any suitable computing device or combination of devices, such as a desktop computer, a laptop computer, a smartphone, a tablet computer, a wearable computer, a server computer, a virtual machine being executed by a physical computing device, and so on. The computing device 1350 and/or server 1352 can also reconstruct images from the data.

In some embodiments, ultrasound data source 1302 can be any suitable source of image data (e.g., measurement data, images reconstructed from measurement data), such as an ultrasound, another computing device (e.g., a server storing image data), and so on. In some embodiments, ultrasound data source 1302 can be local to computing device 1350. For example, ultrasound data source 1302 can be incorporated with computing device 1350 (e.g., computing device 1350 can be configured as part of a device for capturing, scanning, and/or storing images). As another example, ultrasound data source 1302 can be connected to computing device 1350 by a cable, a direct wireless link, and so on. Additionally or alternatively, in some embodiments, ultrasound data source 1302 can be located locally and/or remotely from computing device 1350, and can communicate data to computing device 1350 (and/or server 1352) via a communication network (e.g., communication network 1354).

In some embodiments, communication network 1354 can be any suitable communication network or combination of communication networks. For example, communication network 1354 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 1354 can be a local area network, a wide area network, a public network (e.g., the Internet), a private or semi-private network (e.g., a corporate or university intranet), any other suitable type of network, or any suitable combination of networks. Communications links shown in FIG. 13 can each be any suitable communications link or combination of communications links, such as wired links, fiber optic links, Wi-Fi links, Bluetooth links, cellular links, and so on.

Figure 14:
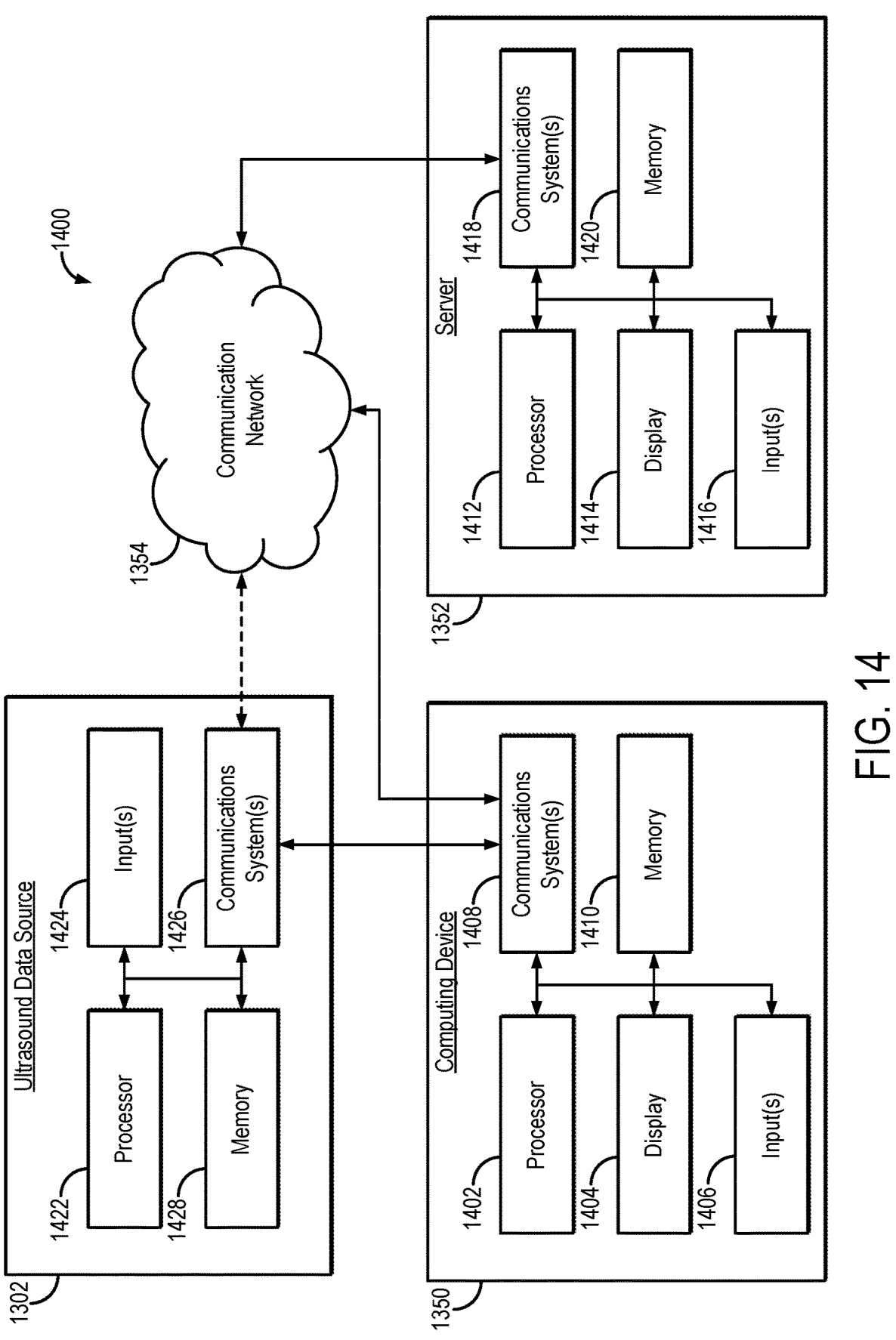
FIG. 14 is a block diagram illustrating example components of the system of FIG. 13.

Referring now to FIG. 14, an example of hardware 1400 that can be used to implement ultrasound data source 1302, computing device 1350, and server 1352 in accordance with some embodiments of the systems and methods described in the present disclosure is shown. As shown in FIG. 14, in some embodiments, computing device 1350 can include a processor 1402, a display 1404, one or more inputs 1406, one or more communication systems 1408, and/or memory 1410. In some embodiments, processor 1402 can be any suitable hardware processor or combination of processors, such as a central processing unit ("CPU"), a graphics processing unit ("GPU"), and so on. In some embodiments, display 1404 can include any suitable display devices, such as a computer monitor, a touchscreen, a television, and so on. In some embodiments, inputs 1406 can include any suitable input devices and/or sensors that can be used to receive user input, such as a keyboard, a mouse, a touchscreen, a microphone, and so on.

In some embodiments, communications systems 1408 can include any suitable hardware, firmware, and/or software for communicating information over communication network 1354 and/or any other suitable communication networks. For example, communications systems 1408 can include one or more transceivers, one or more communication chips and/or chip sets, and so on. In a more particular example, communications systems 1408 can include hardware, firmware and/or software that can be used to establish a Wi-Fi connection, a Bluetooth connection, a cellular connection, an Ethernet connection, and so on.

In some embodiments, memory 1410 can include any suitable storage device or devices that can be used to store instructions, values, data, or the like, that can be used, for example, by processor 1402 to present content using display 1404, to communicate with server 1352 via communications system(s) 1408, and so on. Memory 1410 can include any suitable volatile memory, non-volatile memory, storage, or any suitable combination thereof. For example, memory 1410 can include RAM, ROM, EEPROM, one or more flash drives, one or more hard disks, one or more solid state drives, one or more optical drives, and so on. In some embodiments, memory 1410 can have encoded thereon, or otherwise stored therein, a computer program for controlling operation of computing device 1350. In such embodiments, processor 1402 can execute at least a portion of the computer program to present content (e.g., images, user interfaces, graphics, tables), receive content from server 1352, transmit information to server 1352, and so on.

In some embodiments, server 1352 can include a processor 1412, a display 1414, one or more inputs 1416, one or more communications systems 1418, and/or memory 1420. In some embodiments, processor 1412 can be any suitable hardware processor or combination of processors, such as a CPU, a GPU, and so on. In some embodiments, display 1414 can include any suitable display devices, such as a computer monitor, a touchscreen, a television, and so on. In some embodiments, inputs 1416 can include any suitable input devices and/or sensors that can be used to receive user input, such as a keyboard, a mouse, a touchscreen, a microphone, and so on.

In some embodiments, communications systems 1418 can include any suitable hardware, firmware, and/or software for communicating information over communication network 1354 and/or any other suitable communication networks. For example, communications systems 1418 can include one or more transceivers, one or more communication chips and/or chip sets, and so on. In a more particular example, communications systems 1418 can include hardware, firmware and/or software that can be used to establish a Wi-Fi connection, a Bluetooth connection, a cellular connection, an Ethernet connection, and so on.

In some embodiments, memory 1420 can include any suitable storage device or devices that can be used to store instructions, values, data, or the like, that can be used, for example, by processor 1412 to present content using display 1414, to communicate with one or more computing devices 1350, and so on. Memory 1420 can include any suitable volatile memory, non-volatile memory, storage, or any suitable combination thereof. For example, memory 1420 can include RAM, ROM, EEPROM, one or more flash drives, one or more hard disks, one or more solid state drives, one or more optical drives, and so on. In some embodiments, memory 1420 can have encoded thereon a server program for controlling operation of server 1352. In such embodiments, processor 1412 can execute at least a portion of the server program to transmit information and/or content (e.g., data, images, a user interface) to one or more computing devices 1350, receive information and/or content from one or more computing devices 1350, receive instructions from one or more devices (e.g., a personal computer, a laptop computer, a tablet computer, a smartphone), and so on.

In some embodiments, ultrasound data source 1302 can include a processor 1422, one or more inputs 1424, one or more communications systems 1426, and/or memory 1428. In some embodiments, processor 1422 can be any suitable hardware processor or combination of processors, such as a CPU, a GPU, and so on. In some embodiments, the one or more input(s) 1424 are generally configured to acquire data, images, or both, and can include an ultrasound system. Additionally or alternatively, in some embodiments, one or more input(s) 1424 can include any suitable hardware, firmware, and/or software for coupling to and/or controlling operations of an ultrasound system. In some embodiments, one or more portions of the one or more input(s) 1424 can be removable and/or replaceable.

Note that, although not shown, ultrasound data source 1302 can include any suitable inputs and/or outputs. For example, ultrasound data source 1302 can include input devices and/or sensors that can be used to receive user input, such as a keyboard, a mouse, a touchscreen, a microphone, a trackpad, a trackball, and so on. As another example, ultrasound data source 1302 can include any suitable display devices, such as a computer monitor, a touchscreen, a television, etc., one or more speakers, and so on.

In some embodiments, communications systems 1426 can include any suitable hardware, firmware, and/or software for communicating information to computing device 1350 (and, in some embodiments, over communication network 1354 and/or any other suitable communication networks). For example, communications systems 1426 can include one or more transceivers, one or more communication chips and/or chip sets, and so on. In a more particular example, communications systems 1426 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 1428 can include any suitable storage device or devices that can be used to store instructions, values, data, or the like, that can be used, for example, by processor 1422 to control the one or more input(s) 1424, and/or receive data from the one or more input(s) 1424; to images from data; present content (e.g., images, a user interface) using a display; communicate with one or more computing devices 1350; and so on. Memory 1428 can include any suitable volatile memory, non-volatile memory, storage, or any suitable combination thereof. For example, memory 1428 can include RAM, ROM, EEPROM, one or more flash drives, one or more hard disks, one or more solid state drives, one or more optical drives, and so on. In some embodiments, memory 1428 can have encoded thereon, or otherwise stored therein, a program for controlling operation of ultrasound data source 1302. In such embodiments, processor 1422 can execute at least a portion of the program to generate images, transmit information and/or content (e.g., data, images) to one or more computing devices 1350, receive information and/or content from one or more computing devices 1350, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. A method for generating an image that depicts blood flow in a subject from ultrasound data acquired using an ultrasound imaging system, the method comprising:

(a) accessing ultrasound data acquired from a subject with the ultrasound imaging system;

(b) generating a plurality of weighted ultrasound data sets, each weighted ultrasound data set being generated by applying a different weighting function to the ultrasound data, wherein each different weighting function applies a different spatial weighting to the ultrasound data such that each weighted ultrasound data set comprises a spatial subset of the ultrasound data localized to a spatial region defined by the respective weighting function;

(c) estimating blood flow signal data for each weighted ultrasound data set by separately tissue clutter filtering each of the weighted ultrasound data sets; and (d) generating a blood flow image from the estimated blood flow signal data by combining the blood flow signal data from the plurality of weighted ultrasound data sets, wherein the blood flow image depicts blood flow in the subject.

2. The method of claim 1, wherein generating the blood flow image comprises generating combined blood flow signal data by combining the blood flow signal data from the plurality of different weighted ultrasound data sets and generating the blood flow image from the combined blood flow signal data.

3. The method of claim 2, wherein generating the combined blood flow signal data comprises weighting each blood flow signal data by a weight before combining the blood flow signal data from the plurality of different weighted ultrasound data sets.

4. The method of claim 3, wherein each blood flow signal data is weighted by a different weight.

5. The method of claim 3, wherein the weight applied to a respective one of the blood flow signal data is dependent on at least one of an intensity of the respective one of the blood flow signal data, a power of the respective one of the blood flow signal data, or a velocity of the respective one of the blood flow signal data.

6. The method of claim 1, wherein generating the blood flow image comprises generating a different blood flow image from the blood flow signal data from each of the plurality of different weighted ultrasound data sets and combining the different blood flow images to generate the blood flow image.

7. The method of claim 6, wherein combining the different blood flow images to generate the blood flow image comprises weighting each different blood flow image by a weight before combining the different blood flow images to generate the blood flow image.

8. The method of claim 7, wherein each different blood flow image is weighted by a different weight.

9. The method of claim 7, wherein the weight applied to a respective one of the different blood flow images is dependent on at least one of an intensity of the respective one of the different blood flow images, a power of the respective one of the different blood flow images, or a velocity of the respective one of the different blood flow images.

10. The method of claim 1, wherein each different weighting function comprises one of a Gaussian window, a triangular window, a Welch window, a sine window, or a Hamming window.

11. The method of claim 1, wherein the tissue clutter filtering is based on an eigenvalue decomposition of each weighted ultrasound data set.

12. The method of claim 1, wherein the tissue clutter filtering is based on a singular value decomposition of each weighted ultrasound data set.

* * * * *